(12) United States Patent  
Moinet et al.

(10) Patent No.: US 7,371,774 B2
(45) Date of Patent: May 13, 2008

(54) BENZOFURANS AND BENZOTHIOPHENES

(75) Inventors: Gérard Moinet, Orsay (FR); Caroline Leriche, Paris (FR); Micheline Kergoat, Bures-sur-Yvette (FR)

(73) Assignee: Merck Patent GmbH, Darmstadt (DE)

( * ) Notice: Subject to any disclaimer, the term of this patent is extended or adjusted under 35 U.S.C. 154(b) by 4 days.

(21) Appl. No.: 10/579,996

(22) PCT Filed: Nov. 8, 2004

(86) PCT No.: PCT/EP2004/012620

§ 371 (c)(1),
(2), (4) Date: May 19, 2006

(87) PCT Pub. No.: WO2005/054226

PCT Pub. Date: Jun. 16, 2005

(65) Prior Publication Data

US 2007/0066680 A1 Mar. 22, 2007

(30) Foreign Application Priority Data

Nov. 20, 2003 (FR) .................................. 03 13615

(51) Int. Cl.
*A61K 31/343* (2006.01)
*A61K 31/381* (2006.01)
*C07D 333/64* (2006.01)
*C07D 307/83* (2006.01)

(52) U.S. Cl. .................. 514/443; 549/51; 549/469; 514/470

(58) Field of Classification Search .................. 549/51, 549/469; 514/443, 470
See application file for complete search history.

(56) References Cited

FOREIGN PATENT DOCUMENTS

WO WO 99/58519 A1 * 11/1999

WO WO 9958519 11/1999

OTHER PUBLICATIONS

Pouzet et al, "Synthesis of (4-Chlorophenyl)-1-oxo-1l4-benzo[b]thien-2-yl)methanone and study of its reactivity towards sulfu- and oxygen-containing nucleophiles," Tetrahedron (1998), vol. 54 (49), pp. 14811-14824.*

J.D. Brewer et al: Annelated furans. VI. Diels-Alder addition to 3-methoxy-2-vinylbenzofurans Australian Journal of Chemistry, vol. 24, No. 9, 1971, pp. 1883-1898, XP009028907.

* cited by examiner

*Primary Examiner*—Kamal A. Saeed
*Assistant Examiner*—Janet L. Coppins
(74) *Attorney, Agent, or Firm*—Millen, White, Zelano, Branigan, P.C.

(57) ABSTRACT

The invention relates to compounds of the general formula (I) below:

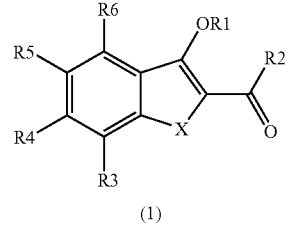

in which R1, R2, R3, R4, R5, R6 and X are as defined in claim 1.

These compounds can be used in the treatment of pathologies associated with insulin resistance syndrome.

27 Claims, No Drawings

BENZOFURANS AND BENZOTHIOPHENES

The present invention relates to variously substituted benzofuran and benzothiophene derivatives that are useful in the treatment of pathologies associated with insulin resistance syndrome.

The present invention relates to compounds of the general formula (I):

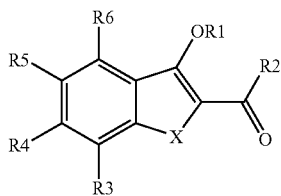

and also the stereoisomers thereof, and the racemates and pharmaceutically acceptable salts thereof,
X=O or S;
R1 is chosen from:
 Alk-COOH,
 Alk-C(=O)—(O)$_m$—Ar,
 Alk-C(=O)—(O)$_m$-Het,
 Alk-C(=O)—(O)$_m$-Alk,
 Alk-C(=O)—(O)$_m$-cycloalkyl,
 Alk-C(=O)NRR',
 Alk-(O)$_m$—Ar,
 Alk-O-Alk,
 Alk-O-Alk-Ar,
 Alk-O-Het;
R2 is chosen from -Alk, —Ar and -cycloalkyl;
R3, R4, R5 and R6, which may be identical or different, are chosen independently from H, -Hal, —OH, -Alk, —OAlk, —CN, —CF$_3$, —NRR' and —NO$_2$;

in which, in the definitions of R1-R6:

each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;

each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;
R and R' are chosen independently from H and Alk;
m=0 or 1;

with the exception of the compounds for which:
 1) R1=—CH$_2$—C(=O)Me, R2=-Me, X=O, R3, R5=H and each R4, R6=H or OMe;
X=O or S;
R1 is chosen from:
 Alk-COOH,
 Alk-C(=O)—(O)$_m$—Ar,
 Alk-C(=O)—(O)$_m$-Het,
 Alk-C(=O)—(O)$_m$-Alk,
 Alk-C(=O)—(O)$_m$-cycloalkyl,
 Alk-C(=O)NRR',
 Alk-(O)$_m$—Ar,
 Alk-O-Alk,
 Alk-O-Alk-Ar,
 Alk-O-Het,
R2 represents —Ar or -cycloalkyl;
R3, R4, R5 and R6, which may be identical or different, are chosen Independently from H, -Hal, —OH, -Alk, —OAlk, —CN, —CF$_3$, —NRR' and —NO$_2$;

in which, in the definitions of R1-R6:

each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;

each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;
R and R' are chosen independently from H and Alk;
m=0 or 1;
X=S;
R1 is chosen from:
 Alk-COOH,
 Alk-C(=O)—(O)$_m$—Ar,
 Alk-C(=O)—(O)$_m$-Het,
 Alk-C(=O)—(O)$_m$-Alk,
 Alk-C(=O)—(O)$_m$-cycloalkyl,
 Alk-C(=O)NRR',
 Alk-(O)$_m$—Ar,
 Alk-O-Alk,
 Alk-O-Alk-Ar,
 Alk-O-Het,
R2 is chosen from -Alk, —Ar and -cycloalkyl;
R3, R4, R5 and R6, which may be identical or different, are chosen independently from H, -Hal, —OH, -Alk, —OAlk, —CN, —CF$_3$, —NRR' and —NO$_2$;

in which, in the definitions of R1-R6:

each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;

each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;
R and R' are chosen independently from H and Alk;
m=0 or 1.

Preferably, R3, R4, R5, R6=H.
Preferably, X=S.
Preferably, R2=Ar optionally substituted by —CN or —COOH; or alkyl optionally substituted by —COOH.
Preferably, R2=phenyl optionally substituted by —CN or —COOH, preferably —CN.
Preferably, m=0.
Preferably, R1=—CH$_2$—COOH, —CH$_2$—C(=O)—(O)$_m$—Ar, —CH$_2$—C(=O)—(O)$_m$-Het, —CH$_2$—C(=O)—(O)$_m$-Alk, —CH$_2$—C(=O)NRR', —CH$_2$—(O)$_m$—Ar, —CH$_2$—O-Alk, —CH$_2$—O-Alk-Ar or —CH$_2$—O-Het,
in which Ar, preferably phenyl, is optionally substituted by one or more groups chosen from Hal, —OAlk, —Ar, -Alk, —O-Alk-Ar, —C(=O)—(O)$_m$-Alk, -Alk-C(=O)—(O)$_m$Alk, —S(O)$_n$—Ar, —S(O)$_n$-Alk, —O—CF$_3$, —CN and —OH, in which m=0 or 1, n=2.

Even more preferably, R1=—CH$_2$—C(=O)—Ar, —CH$_2$—C(=O)-Alk or —(CH$_2$)$_{m'}$—(O)$_m$—Ar, in which Ar, preferably phenyl, is optionally substituted by one or more groups chosen from Hal, —OAlk, —Ar, -Alk, —O-Alk-Ar, —C(=O)—(O)$_m$-Alk, -Alk-C(=O)—(O)$_m$Alk, —S(O)$_n$—Ar, —S(O)$_n$-Alk, —O—CF$_3$, —CN and —OH, in which m=0 or 1, m'=1 or 2, n=2.

Preferably, m'=2 if m=1.

Advantageously, R1=—CH$_2$—C(=O)-Alk, in which, preferably, Alk=-CMe$_3$.

Advantageously, R1=—CH$_2$—C(=O)-phenyl or —CH$_2$-phenyl in which phenyl is optionally substituted by one or more groups chosen from -Hal, —OAlk, —CN, —SO$_2$Alk and -Alk.

The compounds of the formula (I) may especially be chosen from:

2-(2-benzoylbenzo[b]thiophen-3-yloxy)-1-(4-chlorophenyl)ethanone;
2-(2-benzoylbenzo[b]thiophen-3-yloxy)-1-phenylethanone;
2-(2-benzoylbenzo[b]thiophen-3-yloxy)-1-(2-methoxyphenyl)ethanone;
2-(2-benzoylbenzo[b]thiophen-3-yloxy)-1-biphenyl-4-ylethanone;
2-(2-benzoylbenzo[b]thiophen-3-yloxy)-1-p-tolylethanone;
2-(2-benzoylbenzo[b]thiophen-3-yloxy)-1-(4-methoxyphenyl)ethanone;
2-(2-benzoylbenzo[b]thiophen-3-yloxy)-1-(4-fluorophenyl)ethanone;
2-(2-benzoylbenzo[b]thiophen-3-yloxy)-1-(3-methoxyphenyl)ethanone;
methyl 2-(2-benzoylbenzo[b]thiophen-3-yloxy)-3-methoxypropionate;
2-(2-benzoylbenzo[b]thiophen-3-yloxy)-1-(2-benzyloxyphenyl)ethanone;
2-(2-benzoylbenzo[b]thiophen-3-yloxy)-1-(4-benzyloxyphenyl)ethanone;
2-(2-benzoylbenzo[b]thiophen-3-yloxy)-1-(3,4-dimethoxyphenyl)ethanone;
2-(2-benzoylbenzo[b]thiophen-3-yloxy)-1-phenylpropan-1-one;
2-(2-benzoylbenzo[b]thiophen-3-yloxy)-1-(2,4-dimethoxyphenyl)ethanone;
1-(2-benzoylbenzo[b]thiophen-3-yloxy)-3,3-dimethylbutan-2-one;
2-(2-benzoylbenzo[b]thiophen-3-yloxy)-1-naphthalen-2-ylethanone;
2-(2-benzoylbenzo[b]thiophen-3-yloxy)-1-(2,3-dichloro-4-methoxyphenyl)ethanone;
2-(2-benzoylbenzo[b]thiophen-3-yloxy)-1-(4-benzyloxy-3-methoxyphenyl)ethanone;
2-(2-benzoylbenzo[b]thiophen-3-yloxy)-1-(2-benzyloxy-5-fluorophenyl)ethanone;
(3-hydroxybenzo[b]thiophen-2-yl)phenylmethanone;
2-(2-benzoylbenzo[b]thiophen-3-yloxy)acetamide;
{3-[2-(4-fluorophenoxy)ethoxy]benzo[b]thiophen-2-yl}phenylmethanone;
(3-phenethyloxybenzo[b]thiophen-2-yl)phenylmethanone;
methyl 3-{4-[2-(2-benzoylbenzo[b]thiophen-3-yloxy)ethoxy]phenyl}propionate;
{3-[2-(naphthalen-1-yloxy)ethoxy]benzo[b]thiophen-2-yl}phenyl methanone;
{3-[2-(2-methoxyphenoxy)ethoxy]benzo[b]thiophen-2-yl}phenyl methanone;
1-{4-[2-(2-benzoylbenzo[b]thiophen-3-yloxy)ethyl]phenyl}ethanone;
ethyl 2-(2-benzoylbenzo[b]thiophen-3-yloxy)-4-phenylbutyrate;
[3-(3-phenoxypropoxy)benzo[b]thiophen-2-yl]phenyl methanone;
[3-(4-tert-butylbenzyloxy)benzo[b]thiophen-2-yl]phenylmethanone;
[3-(2-benzenesulfonylmethylbenzyloxy)benzo[b]thiophen-2-yl]phenyl methanone;
methyl 4-(2-benzoylbenzo[b]thiophen-3-yloxymethyl)benzoate;
phenyl[3-(4-trifluoromethoxybenzyloxy)benzo[b]thiophen-2-yl]methanone;
[3-(biphenyl-2-ylmethoxy)benzo[b]thiophen-2-yl]phenylmethanone;
[3-(4-methylbenzyloxy)benzo[b]thiophen-2-yl]phenylmethanone;
(3-benzyloxybenzo[b]thiophen-2-yl)phenylmethanone;
[3-(2,3-difluorobenzyloxy)benzo[b]thiophen-2-yl]phenylmethanone;
sodium 2-(4-cyanobenzoyl)benzo[b]thiophen-3-olate;
4-[3-(2-chloro-4-fluorobenzyloxy)benzo[b]thiophene-2-carbonyl]benzonitrile;
4-[3-(3,4-dichlorobenzyloxy)benzo[b]thiophene-2-carbonyl]benzonitrile;
4-[3-(3-trifluoromethyl benzyloxy)benzo[b]thiophene-2-carbonyl]benzonitrile;
4-[3-(2-cyanobenzyloxy)benzo[b]thiophene-2-carbonyl]benzonitrile;
4-[3-(3-cyanobenzyloxy)benzo[b]thiophene-2-carbonyl]benzonitrile;
4-[3-(4-cyanobenzyloxy)benzo[b]thiophene-2-carbonyl]benzonitrile;
4-[3-(3,5-bis-trifluoromethyl benzyloxy)benzo[b]thiophene-2-carbonyl]benzonitrile;
methyl 4-[2-(4-cyanobenzoyl)benzo[b]thiophen-3-yloxymethyl]benzoate;
4-[3-(4-fluoro-2-trifluoromethylbenzyloxy)benzo[b]thiophene-2-carbonyl]benzonitrile;
4-(3-pentafluorophenylmethoxybenzo[b]thiophene-2-carbonyl)benzonitrile;
4-[3-(2,6-difluorobenzyloxy)benzo[b]thiophene-2-carbonyl]benzonitrile;
4-[3-(4-trifluoromethylbenzyloxy)benzo[b]thiophene-2-carbonyl]benzonitrile;
4-[3-(2-chlorobenzyloxy)benzo[b]thiophene-2-carbonyl]benzonitrile;
4-[3-(biphenyl-2-yl methoxy)benzo[b]thiophene-2-carbonyl]benzonitrile;
4-[3-(4-bromo-2-fluorobenzyloxy)benzo[b]thiophene-2-carbonyl]benzonitrile;
4-[3-(2-methylbenzyloxy)benzo[b]thiophene-2-carbonyl]benzonitrile;
4-[3-(2,6-dichlorobenzyloxy)benzo[b]thiophene-2-carbonyl]benzonitrile;
4-[3-(3-chlorobenzyloxy)benzo[b]thiophene-2-carbonyl]benzonitrile;
4-[3-(2-bromobenzyloxy)benzo[b]thiophene-2-carbonyl]benzonitrile;
4-[3-(4-bromobenzyloxy)benzo[b]thiophene-2-carbonyl]benzonitrile;
4-(3-benzyloxybenzo[b]thiophene-2-carbonyl)benzonitrile;

4-[3-(3-bromobenzyloxy)benzo[b]thiophene-2-carbonyl]
benzonitrile;
4-[3-(2,5-difluorobenzyloxy)benzo[b]thiophene-2-carbonyl]benzonitrile;
4-[3-(3,4-difluorobenzyloxy)benzo[b]thiophene-2-carbonyl]benzonitrile;
4-[3-(3,5-difluorobenzyloxy)benzo[b]thiophene-2-carbonyl]benzonitrile;
4-[3-(2,4-difluorobenzyloxy)benzo[b]thiophene-2-carbonyl]benzonitrile;
4-[3-(2,3-difluorobenzyloxy)benzo[b]thiophene-2-carbonyl]benzonitrile;
4-[3-(4-methanesulfonylbenzyloxy)benzo[b]thiophene-2-carbonyl]benzonitrile;
4-[3-(4-iodobenzyloxy)benzo[b]thiophene-2-carbonyl]benzonitrile;
4-{3-[2-(4-chlorophenyl)-2-oxoethoxy]benzo[b]thiophene-2-carbonyl}benzonitrile;
4-[3-(2-oxo-2-phenylethoxy)benzo[b]thiophene-2-carbonyl]benzonitrile;
4-{3-[2-(2-methoxyphenyl)-2-oxoethoxy]benzo[b]thiophene-2-carbonyl}benzonitrile;
4-[3-(2-biphenyl-4-yl-2-oxoethoxy)benzo[b]thiophene-2-carbonyl]benzonitrile;
4-[3-(2-oxo-2-p-tolylethoxy)benzo[b]thiophene-2-carbonyl]benzonitrile;
4-{3-[2-(4-methoxyphenyl)-2-oxoethoxy]benzo[b]thiophene-2-carbonyl}benzonitrile;
4-[3-(2-adamantan-1-yl-2-oxoethoxy)benzo[b]thiophene-2-carbonyl]benzonitrile;
4-{3-[2-(4-fluorophenyl)-2-oxoethoxy]benzo[b]thiophene-2-carbonyl}benzonitrile;
4-{3-[2-(3-methoxyphenyl)-2-oxoethoxy]benzo[b]thiophene-2-carbonyl}benzonitrile;
4-{3-[2-(2-benzyloxyphenyl)-2-oxoethoxy]benzo[b]thiophene-2-carbonyl}benzonitrile;
4-{3-[2-(4-benzyloxyphenyl)-2-oxoethoxy]benzo[b]thiophene-2-carbonyl}benzonitrile;
4-{3-[2-(3,4-dimethoxyphenyl)-2-oxoethoxy]benzo[b]thiophene-2-carbonyl}benzonitrile;
4-{3-[2-(2,4-dimethoxyphenyl)-2-oxoethoxy]benzo[b]thiophene-2-carbonyl}benzonitrile;
4-[3-(2-naphthalen-2-yl-2-oxoethoxy)benzo[b]thiophene-2-carbonyl]benzonitrile;
4-{3-[2-(4-benzyloxy-3-methoxyphenyl)-2-oxoethoxy]benzo[b]thiophene-2-carbonyl}benzonitrile;
4-{3-[2-(2-benzyloxy-5-fluorophenyl)-2-oxoethoxy]benzo[b]thiophene-2-carbonyl}-benzonitrile;
(3-hydroxybenzofuran-2-yl)phenylmethanone;
2-(2-benzoylbenzofuran-3-yloxy)-1-(4-chlorophenyl)ethanone;
2-(2-benzoylbenzofuran-3-yloxy)-1-(2-methoxyphenyl)ethanone;
2-(2-benzoylbenzofuran-3-yloxy)-1-biphenyl-4-ylethanone;
2-(2-benzoylbenzofuran-3-yloxy)-1-p-tolylethanone;
2-(2-benzoylbenzofuran-3-yloxy)-1-(4-methoxyphenyl)ethanone;
1-adamantan-1-yl-2-(2-benzoylbenzofuran-3-yloxy)ethanone;
2-(2-benzoylbenzofuran-3-yloxy)-1-(4-fluorophenyl)ethanone;
methyl 2-(2-benzoylbenzofuran-3-yloxy)-3-methoxypropionate;
2-(2-benzoylbenzofuran-3-yloxy)-1-(2-benzyloxyphenyl)ethanone;
2-(2-benzoylbenzofuran-3-yloxy)-1-(4-benzyloxyphenyl)ethanone;
2-(2-benzoylbenzofuran-3-yloxy)-1-(3,4-dimethoxyphenyl)ethanone;
2-(2-benzoylbenzofuran-3-yloxy)-1-(2,4-dimethoxyphenyl)ethanone;
2-(2-benzoylbenzofuran-3-yloxy)-1-naphthalen-2-ylethanone;

and also the stereoisomeric forms and the racemates thereof, and the pharmaceutically acceptable salts.

The compounds of the formula (I) are preferably chosen from:
2-(2-benzoylbenzo[b]thiophen-3-yloxy)-1-(4-chlorophenyl)ethanone;
2-(2-benzoylbenzo[b]thiophen-3-yloxy)-1-(2-methoxyphenyl)ethanone;
2-(2-benzoylbenzo[b]thiophen-3-yloxy)-1-(2,4-dimethoxyphenyl)ethanone;
1-(2-benzoylbenzo[b]thiophen-3-yloxy)-3,3-dimethylbutan-2-one;
4-[3-(2-cyanobenzyloxy)benzo[b]thiophene-2-carbonyl]benzonitrile;
4-[3-(3-cyanobenzyloxy)benzo[b]thiophene-2-carbonyl]benzonitrile;
4-[3-(2,6-dichlorobenzyloxy)benzo[b]thiophene-2-carbonyl]benzonitrile;
4-(3-benzyloxybenzo[b]thiophene-2-carbonyl)benzonitrile;
4-[3-(4-methanesulfonylbenzyloxy)benzo[b]thiophene-2-carbonyl]benzonitrile;
4-[3-(2-oxo-2-phenylethoxy)benzo[b]thiophene-2-carbonyl]benzonitrile;
4-{3-[2-(2-methoxyphenyl)-2-oxoethoxy]benzo[b]thiophene-2-carbonyl}benzonitrile;
4-[3-(2-oxo-2-p-tolylethoxy)benzo[b]thiophene-2-carbonyl]benzonitrile;

and also the stereoisomeric forms and the racemates thereof, and the pharmaceutically acceptable salts.

Even more preferably, the compounds of the formula (I) are chosen from:
1-(2-benzoylbenzo[b]thiophen-3-yloxy)-3,3-dimethylbutan-2-one;

and also the stereoisomeric forms and the racemates thereof, and the pharmaceutically acceptable salts.

According to the present invention, the radical -Alk represents an alkyl radical, i.e. a straight-chain or branched-chain saturated hydrocarbon-based radical, of 1 to 20 carbon atoms and preferably of 1 to 5 carbon atoms.

If they are linear, mention may be made especially of methyl, ethyl, propyl, butyl, pentyl, hexyl, octyl, nonyl, decyl, dodecyl, hexadecyl and octadecyl radicals.

If they are branched or substituted by one or more alkyl radicals, mention may be made especially of isopropyl, tert-butyl, 2-ethylhexyl, 2-methylbutyl, 2-methylpentyl, 1-methylpentyl and 3-methylheptyl radicals.

Among the halogen atoms, denoted by Hal, mention is made more particularly of fluorine, chlorine, bromine and iodine atoms, preferably fluorine.

The cycloalkyl radical is a mono-, bi- or tricyclic, saturated or partially unsaturated, non-aromatic hydrocarbon-based radical of 3 to 10 carbon atoms, such as, especially, cyclopropyl, cyclopentyl, cyclohexyl or adamantyl, and also the corresponding rings containing one or more unsaturations.

Ar denotes an aryl radical, i.e. a mono or bicyclic hydrocarbon-based aromatic system of 6 to 10 carbon atoms.

Among the aryl radicals, mention may be made especially of the phenyl or naphthyl radical, more particularly substituted by at least one halogen atom.

Among the -AlkAr (-alkylaryl) radicals, mention may be made especially of the benzyl or phenethyl radical.

Het represents a heteroaryl radical, i.e. a mono- or bicyclic aromatic system of 5 to 10 carbon atoms, comprising one or more hetero atoms chosen from nitrogen, oxygen and sulfur. Among the heteroaryl radicals, mention may be made of pyrazinyl, thienyl, oxazolyl, furazanyl, pyrrolyl, 1,2,4-thiadiazolyl, naphthyridinyl, pyridazinyl, quinoxalinyl, phthalazinyl, imidazo[1,2-a]pyridyl, imidazo[2,1-b]thiazolyl, cinnolinyl, triazinyl, benzofurazanyl, azaindolyl, benzimidazolyl, benzothienyl, thienopyridyl, thienopyrimidinyl, pyrrolopyridyl, imidazopyridyl, benzazaindolyl, 1,2,4-triazinyl, benzothiazolyl, furanyl, imidazolyl, indolyl, triazolyl, tetrazolyl, indolizinyl, isoxazolyl, isoquinolyl, isothiazolyl, oxadiazolyl, pyrazinyl, pyridazinyl, pyrazolyl, pyridyl, pyrimidinyl, purinyl, quinazolinyl, quinolyl, isoquinolyl, 1,3,4-thiadiazolyl, thiazolyl, triazinyl, isothiazolyl and carbazolyl, and also the corresponding groups derived from their fusion or from fusion with the phenyl nucleus. The preferred heteroaryl groups include thienyl, pyrrolyl, quinoxalinyl, furanyl, imidazolyl, indolyl, isoxazolyl, isothiazolyl, pyrazinyl, pyridazinyl, pyrazolyl, pyridyl, pyrimidinyl, quinazolinyl, quinolinyl, thiazolyl, carbazolyl and thiadiazolyl, and groups derived from fusion with a phenyl nucleus, and more particularly quinolinyl, carbazolyl and thiadiazolyl.

The expression "pharmaceutically acceptable salts" refers to the relatively non-toxic mineral and organic acid-addition salts, and the base-addition salts, of the compounds of the present invention. These salts can be prepared in situ during the final isolation and purification of the compounds. In particular, the acid-addition salts can be prepared by separately reacting the purified compound in its purified form with an organic or mineral acid and isolating the salt thus formed. Among the examples of acid-addition salts are the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, sulfamates, malonates, salicylates, propionates, methylenebis-b-hydroxynaphthoates, gentisic acid, isethionates, di-p-toluoyltartrates, methanesulfonates, ethanesulfonates, benzenesulfonates, p-toluenesulfonates, cyclohexyl sulfamates and quinates-laurylsulfonate, and analogues. (See for example S. M. Berge et al. "Pharmaceutical Salts" *J. Pharm. Sci,* 66: pp. 1-19 (1977) which is incorporated herein by reference). The acid-addition salts can also be prepared by separately reacting the purified compound in its acid form with an organic or mineral base and isolating the salt thus formed. The acid-addition salts include amine salts and metal salts. The suitable metal salts include the sodium, potassium, calcium, barium, zinc, magnesium and aluminium salts. The sodium and potassium salts are preferred. The suitable mineral base-addition salts are prepared from metallic bases including sodium hydride, sodium hydroxide, potassium hydroxide, calcium hydroxide, aluminium hydroxide, lithium hydroxide, magnesium hydroxide and zinc hydroxide. The suitable amine base-addition salts are prepared from amines whose basicity is sufficient to form a stable salt, and preferably include amines that are often used in medicinal chemistry on account of their low toxicity and their acceptability for medical use: ammonia, ethylenediamine, N-methylglucamine, lysine, arginine, ornithine, choline, N,N'-dibenzylethylenediamine, chloroprocaine, diethanolamine, procaine, N-benzyl-phenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, for example lysine and arginine, and dicyclohexylamine, and analogues.

The compounds of the invention of the formula (I) as defined above containing a sufficiently acidic function or a sufficiently basic function, or both, may include the corresponding pharmaceutically acceptable salts of an organic or mineral acid or of an organic or mineral base.

The compounds of the general formula (I) can be prepared by application or adaptation of any method known per se and/or within the capacity of a person skilled in the art, especially those described by Larock in *Comprehensive Organic Transformations*, VCH Pub., 1989, or by application or adaptation of the processes described in the examples that follow.

According to another subject, the invention also relates to the preparation of the compounds of the formula (I) described hereinabove, according to the methodology described hereinbelow.

The compounds of the general formula (I) can especially be prepared according to the synthetic route:

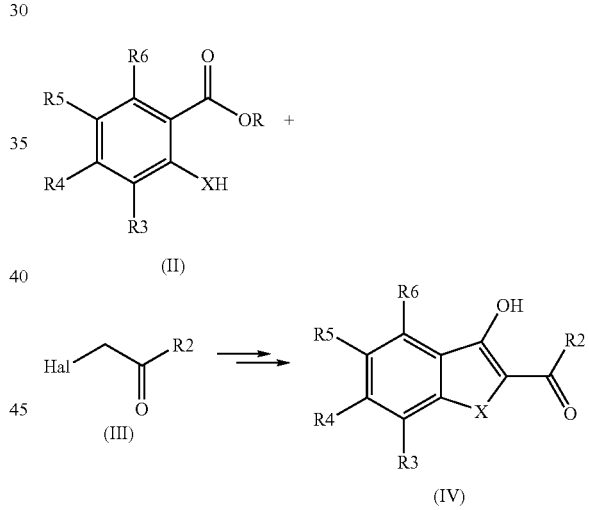

1—Addition of a (thio)salicylic acid derivative of the formula (II)

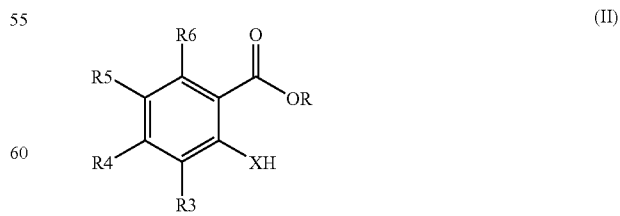

in which R3-R6 and X are as defined above, and R represents a hydrogen atom or an alkyl radical, to a 2-haloethanone derivative of the formula (III):

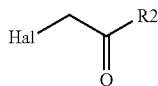

(III)

in which Hal represents a halogen atom and R2 is as defined above, in a polar solvent, such as ethanol, at a temperature of from −20 to 200° C., more particularly 0-20° C., followed by cyclization in a polar solvent, such as methanol, water, DMF, NMP, DMSO or iPrOH, preferably DMF at a temperature of from −20 to 200° C., more particularly 0-200° C., preferably in the presence of sodium acetate, 2—Coupling of the resultant derivative (IV)

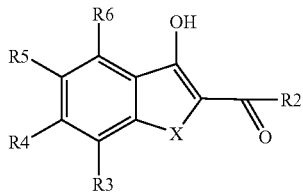

(IV)

with a halo derivative of the formula (V):

Hal-R1          (V)

on an equimolar basis, in a polar solvent, such as ethanol, methanol, water, DMF, NMP, DMSO or iPrOH, preferably DMF, at a temperature of from −20 to 200° C., more particularly 0-200° C.

The mode of addition of a salicylic acid to a 2-bromoacetophenone derivative is described especially by Gayral, Buisson et al. in Eur. J. Med. Chem. Chim. Ther.; FR; 20; 2; 1985; 187-189. The coupling step has been described especially by Blicke in J. Am. Chem. Soc.; EN; 71; 1949; 2856-2858.

The said process may optionally also include the step consisting in isolating the product obtained.

In the reactions described hereinbelow, it may be necessary to protect reactive functional groups, for example hydroxyl, amino, imino, thio or carboxyl groups, if they are desired in the final product, to avoid their unwanted participation in the reactions. The conventional protecting groups can be used in accordance with the standard practice; for examples, see T. W. Green and P. G. M. Wuts in *Protective Groups in Organic Chemistry*, John Wiley and Sons, 1991; J. F. W. McOmie in *Protective Groups in Organic Chemistry*, Plenum Press, 1973.

The compound thus prepared can be recovered from the reaction mixture via the conventional means. For example, the compounds can be recovered by distilling the solvent from the reaction mixture or, if necessary, after distilling off the solvent from the mixture of the solution, pouring the remainder into water, followed by extraction with a water-immiscible organic solvent, and distilling the solvent from the extract. In addition, the product can also be purified, if so desired, by various techniques, such as recrystallization, reprecipitation or various chromatographic techniques, especially column chromatography or preparative thin-layer chromatography.

It will be appreciated that the compounds that are useful according to the present invention may contain asymmetric centres. These asymmetric centres may be, independently, of R or S configuration. It will be apparent to a person skilled in the art that certain compounds that are useful according to the invention may also exhibit geometrical isomerism. It should be understood that the present invention includes individual geometrical isomers and stereoisomers, and mixtures thereof, including racemic mixtures, of compounds of the formula (I) above. These isomers can be separated from their mixtures by application or adaptation of known processes, for example chromatography techniques or recrystallization techniques, or they are prepared separately from suitable isomers of their intermediates.

For the purposes of the present text, it is understood that the tautomeric forms are included in the citation of a given group, for example thio/mercapto or oxo/hydroxyl.

The acid-addition salts are formed with the compounds that are useful according to the invention in which a basic function, such as an amino, alkylamino or dialkylamino group is present. The pharmaceutically acceptable, i.e. non-toxic, acid-addition salts are preferred. The selected salts are optimally chosen so as to be compatible with the usual pharmaceutical vehicles and suitable for oral or parenteral administration. The acid-addition salts of the compounds that are useful according to the present invention can be prepared by reacting the free base with the appropriate acid, by application or adaptation of known processes. For example, the acid-addition salts of the compounds that are useful according to the present invention can be prepared either by dissolving the free base in water or in a basified aqueous solution or suitable solvents comprising the appropriate acid, and isolating the solvent by evaporating the solution, or by reacting the free base and the acid in an organic solvent. In which case the salt separates out directly or maybe obtained by concentrating the solution. Among the acids that are suitable for use in the preparation of these salts are hydrochloric acid, hydrobromic acid, phosphoric acid, sulfuric acid, various organic carboxylic and sulfonic acids, such as acetic acid, citric acid, propionic acid, succinic acid, benzoic acid, tartaric acid, fumaric acid, mandelic acid, ascorbic. acid, malic acid, methanesulfonic acid, toluene-sulfonic acid, fatty acids, adipate, alginate, ascorbate, aspartate, benzenesulfonate, benzoate, cyclopentaneproplonate, digluconate, dodecyl sulfate, bisulfate, butyrate, lactate, laurate, lauryl sulfate, malate, hydriodide, 2-hydroxyethane-sulfonate, glycerophosphate, picrate, pivalate, pamoate, pectinate, persulfate, 3-phenylpropionate, thiocyanate, 2-naphthalenesulfonate, undecanoate, nicotinate, hemisulfate, heptonate, hexanoate, camphorate, camphorsulfonate and the like.

The acid-addition salts of the compounds that are useful according to the present invention can be regenerated from the salts by application or adaptation of known processes. For example, the parent compounds that are useful according to the invention can be regenerated from their acid-addition salts by treatment with an alkali, for example aqueous sodium bicarbonate solution or aqueous ammonia solution.

The compounds that are useful according to the present invention can be regenerated from their base-addition salts by application or adaptation of known processes. For example, the parent compounds that are useful according to the invention can be regenerated from their base-addition salts by treatment with an acid, for example hydrochloric acid.

The base-addition salts can be formed if the compound that is useful according to the invention contains a carboxyl group, or a sufficiently acidic bioisostere. The bases that can be used to prepare the base-addition salts preferably include those that produce, if they are combined with a free acid, pharmaceutically acceptable salts, i.e. salts whose cations are not toxic to the patient in the pharmaceutical doses of the salts, such that the beneficial inhibitory effects intrinsic to the free base are not negated by the side effects attributable to the cations. The pharmaceutically acceptable salts, including those derived from alkaline-earth metal salts, within the scope of the present invention include those derived from the following bases: sodium hydride, sodium hydroxide, potassium hydroxide, calcium hydroxide, aluminium hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide and the like.

The compounds that are useful according to the present invention can be readily prepared, or formed during the process of the invention, in the form of solvates (for example hydrates). The hydrates of the compounds that are useful according to the present invention can be readily prepared by recrystallization of an aqueous/organic solvent mixture, using organic solvents, such as dioxane, tetrahydrofuran or methanol.

The basic products or the intermediates can be prepared by application or adaptation of known processes, for example processes as described in the Reference Examples or obvious chemical equivalents thereof.

According to the present invention, the compounds of the formula (I) have hypoglycaemiant activity. They can reduce hyperglycaemia, more particularly the hyperglycaemia of non-insulin-dependent diabetes.

Insulin resistance is characterized by a reduction in the action of insulin (cf. Presse Médicale, 1997, 26 (No 14), 671-677) and is involved in a large number of pathological conditions, such as diabetes and more particularly non-insulin-dependent diabetes (type II diabetes or NIDDM), dyslipidaemia, obesity and certain microvascular and macrovascular complications, for instance atherosclerosis, arterial hypertension, inflammatory processes, macroangiopathy, microangiopathy, retinopathy and neuropathy.

In this respect, reference will be made, for example, to Diabetes, vol. 37, 1988, 1595-1607; *Journal of Diabetes and Its Complications*, 1998, 12, 110-119 or Horm. Res., 1992, 38, 28-32.

In particular, the compounds of the invention show strong hypoglycaemiant activity.

The compounds of the formula (I) are thus useful in the treatment of hyperglycaemia-related pathologies.

The present invention thus also relates to pharmaceutical compositions comprising, as active principle, a compound according to the invention.

The pharmaceutical compositions according to the invention can be presented in forms intended for parenteral, oral, rectal, permucous or percutaneous administration.

They will thus be presented in the form of injectable solutions or suspensions or multi-dose bottles, in the form of plain or coated tablets, sugar-coated tablets, wafer capsules, gel capsules, pills, cachets, powders, suppositories or rectal capsules, solutions or suspensions, for percutaneous use in a polar solvent, or for permucous use.

The excipients that are suitable for such administrations are cellulose or microcrystalline cellulose derivatives, alkaline-earth metal carbonates, magnesium phosphate, starches, modified starches and lactose for solid forms.

For rectal use, cocoa butter or polyethylene glycol stearates are the preferred excipients.

For parenteral use, water, aqueous solutions, physiological saline and isotonic solutions are the vehicles most appropriately used.

The dosage may vary within wide ranges (0.5 mg to 1000 mg) according to the therapeutic indication and the route of administration, and also to the age and weight of the patient.

In the case of non-insulin-dependent diabetes, in man, hyperglycaemia is the results of two major defects: an impairment in insulin secretion and a reduction in the efficacy of insulin at three sites (liver, muscles and adipose issue).

By increasing insulin secretion by the pancreatic beta cells, the compounds of the present invention are thus capable of improving the glycaemia of non-insulin-dependent diabetic patients.

The examples that follow illustrate the Invention without, however, limiting it.

I. PREPARATION OF THE COMPOUNDS OF THE FORMULA (I)

The starting materials used are known products or are prepared according to known processes.

A—Example of the Preparation of a Compound of the Formula (I)

Preparation of (3-hydroxybenzo[b]thiophen-2-yl)phenylmethanone 32.250 g (0.162 mol) of 2-bromoacetophenone and 13.290 g (0.162 mol) of sodium acetate are added to 25 g (0.162 mol) of thiosalicylic acid $C_7H_6O_2S$ in 200 ml of methanol. The reaction is stirred for one hour at room temperature. The mixture is diluted with water and the compound is filtered off, washed with water and dried to give 44.0 g (0.160 mol, 99.1%) of a white solid (used without further purification for the following step).

26.580 g (0.324 mol) of sodium acetate are added to 44 g (0.162 mol) of the crude product in 200 ml of DMF. The reaction is refluxed for 30 min. The mixture is diluted with water and the precipitate formed is washed with water and dried under vacuum to give 36.1 g of a white solid (0.141 mol, 88%) of the cyclized compound $C_5H_{10}O_2S$.

Preparation of 1-(2-benzoylbenzo[b]thiophen-3-yloxy)-3,3-dimethylbutan-2-one 188.72 mg (4.718 mmol) of NaH (60% suspension) are added to 1 g (3.932 mmol) $C_5H_{10}O_2S$ in 5 ml of DMF. The mixture is stirred for 10 minutes at room temperature and 581.840 μl (4.325 mmol) of 1-bromopinacolone are then added. The mixture is stirred at room temperature for 20 hours, and diluted with water. The product is extracted with ethyl acetate. The organic phases are washed with water and with saturated NaCl solution, dried over $Na_2SO_4$ and then concentrated to give 1.38 g (3.915 mmol, 99%) of a white powder.

By way of example, the compounds listed in table A were prepared according to the procedures described above. Table A collates the formulae and characteristics of the compounds of the formula (I).

TABLE A

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 1 | 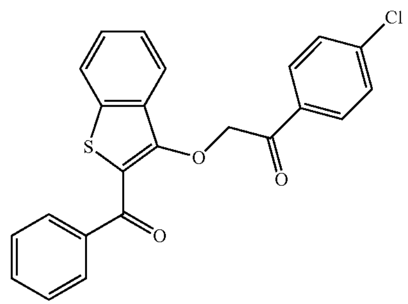 | $C_{23}H_{15}ClO_3S$ | 406.89 | M + 1 = 407 | 85.1 | 4.98 | |
| 2 | 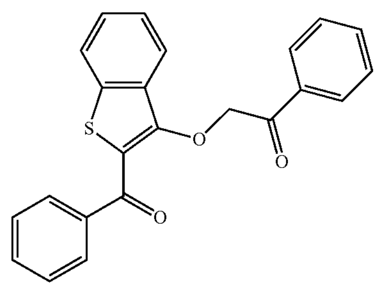 | $C_{23}H_{16}O_3S$ | 372.45 | M + 1 = 373 | 89.6 | 3.34 | |
| 3 | 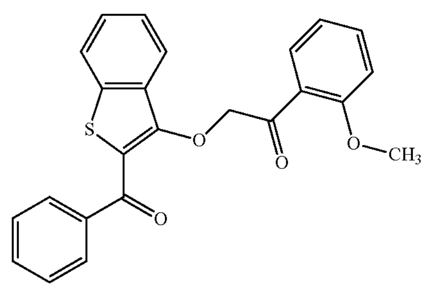 | $C_{24}H_{18}O_4S$ | 402.47 | M + 1 = 403 | 94.1 | 3.76 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 4 | 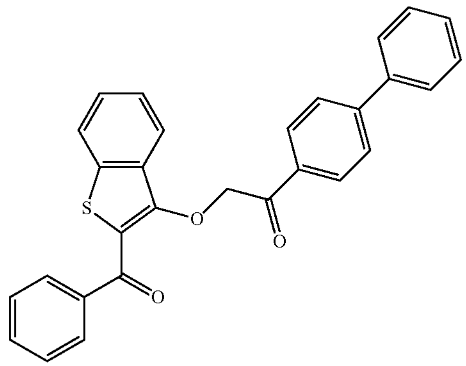 | $C_{29}H_{20}O_3S$ | 448.54 | M + 1 = 449 | 85.7 | | |
| 5 | 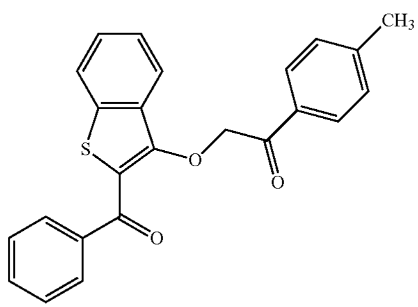 | $C_{24}H_{18}O_3S$ | 386.47 | M + 1 = 387 | 89.2 | 4.36 | |
| 6 | 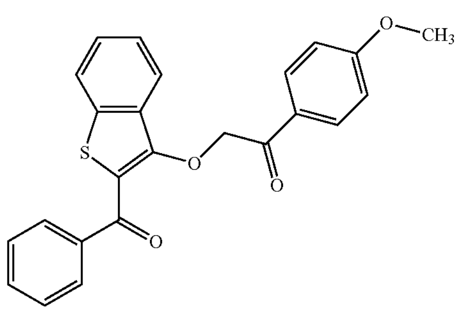 | $C_{24}H_{18}O_4S$ | 402.47 | M + 1 = 403 | 85.9 | 3.41 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 7 | 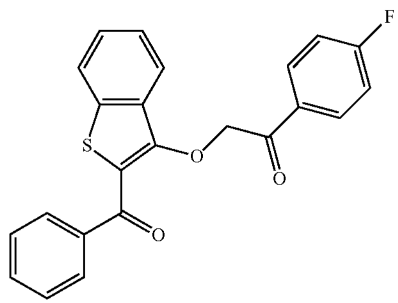 | $C_{23}H_{15}O_3S$ | 390.44 | M + 1 = 391 | 82.8 | 3.54 | |
| 8 | 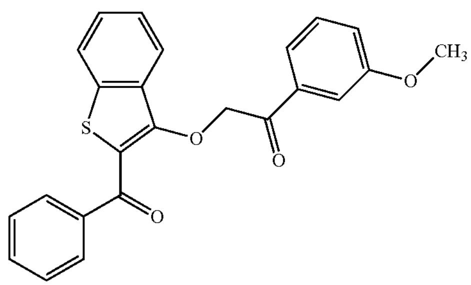 | $C_{24}H_{18}O_4S$ | 402.47 | M + 1 = 403 | 91.3 | 3.82 | |
| 9 | 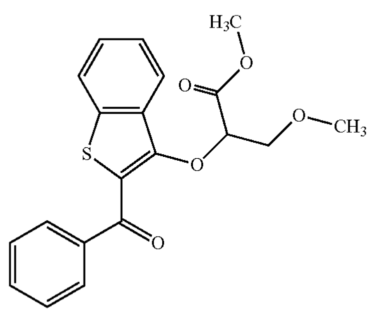 | $C_{20}H_{18}O_5S$ | 370.43 | M + 1 = 371 | 81 | 2.26 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 10 | 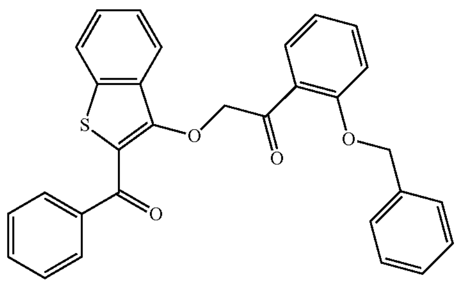 | $C_{30}H_{22}O_4S$ | 478.57 | M + 1 = 479 | 81.3 | 6.29 | |
| 11 | 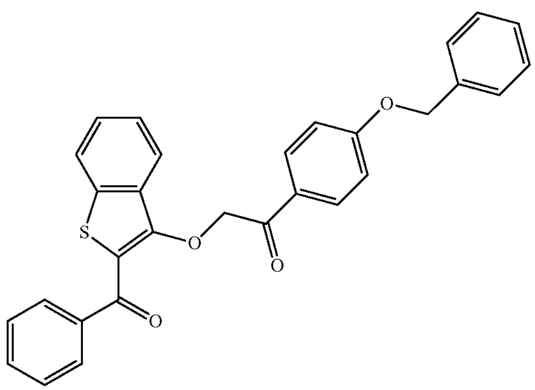 | $C_{30}H_{22}O_4S$ | 478.57 | M + 1 = 479 | 90.1 | 8.74 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 12 | 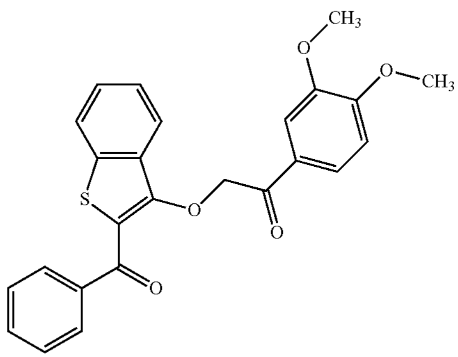 | C$_{25}$H$_{20}$O$_5$S | 432.50 | M + 1 = 433 | 79.8 | 2.74 | |
| 13 | 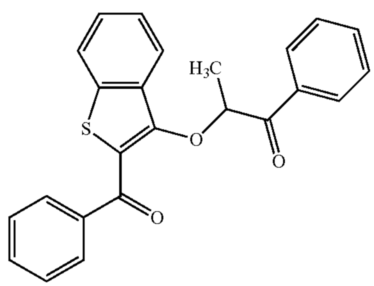 | C$_{24}$H$_{18}$O$_3$S | 386.47 | M + 1 = 387 | 93.9 | 3.75 | |
| 14 | 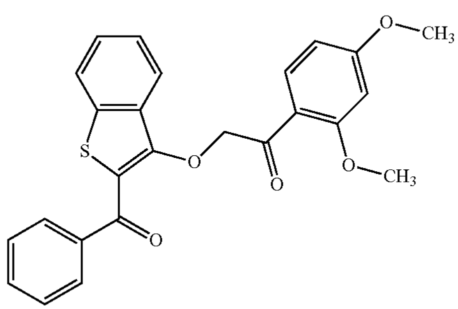 | C$_{25}$H$_{20}$O$_5$S | 432.50 | M + 1 = 433 | 96 | 3.87 | |

TABLE A-continued

Hewlett Packard LC/MSD (Simple Quad)-Orthogonal Spray Source APCI, HP Series 1100 line with diode array

| Products | Structure | Formula | Mol. weight g·mol⁻¹ | MS | Purity (%) | Tr (min) | 1H NMR 200 MHz DMSOd6 (δ ppm) |
|---|---|---|---|---|---|---|---|
| 15 | 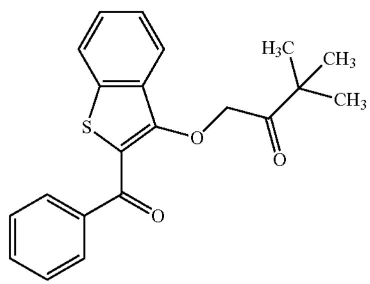 | $C_{21}H_{20}O_3S$ | 352.46 | | 97.5 | 3.26 | |
| 16 | 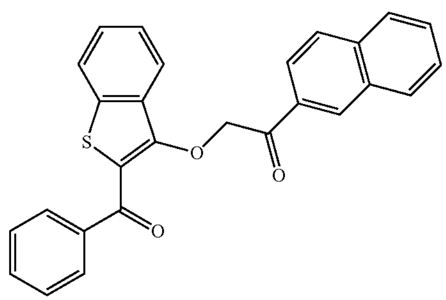 | $C_{27}H_{18}O_3S$ | 422.51 | M + 1 = 423 | 89.2 | 6.23 | |
| 17 | 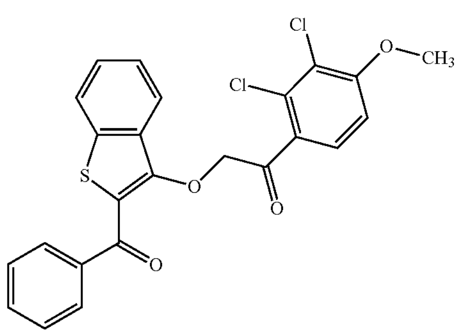 | $C_{24}H_{16}Cl_2O_4S$ | 471.36 | M + 1 = 471 | 88.4 | 6.09 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 18 | 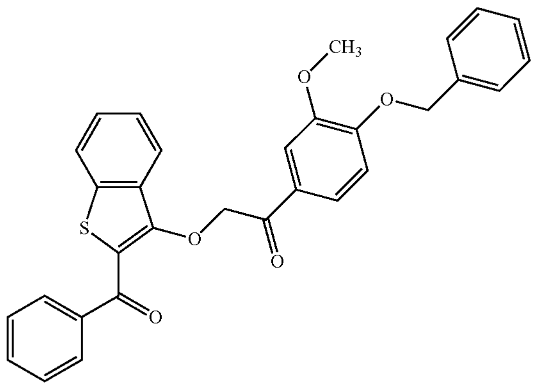 | $C_{31}H_{24}O_5S$ | 508.60 | M + 1 = 509 | 80 | 5.75 | |
| 19 | 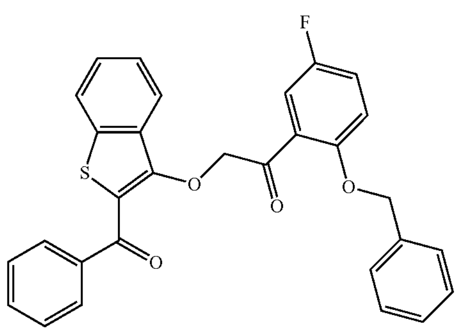 | $C_{30}H_{21}FO_4S$ | 496.56 | M + 1 = 497 | 82 | 7.93 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 20 | benzothiophene with OH and benzoyl | C$_{15}$H$_{10}$O$_2$S | 254.31 | M + 1 = 255 | 99 | | 7.61 (m, 5H) 7.92 (m, 4H) |
| 21 | benzothiophene with OCH$_2$C(O)NH$_2$ and benzoyl | C$_{17}$H$_{13}$NO$_3$S | 311.36 | M + 1 = 312 | 99 | 2.1 | |
| 22 | benzothiophene with O-CH$_2$CH$_2$-O-(4-fluorophenyl) and benzoyl | C$_{23}$H$_{17}$FO$_3$S | 392.45 | M + 1 = 393 | 89.6 | 5.19 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 23 | 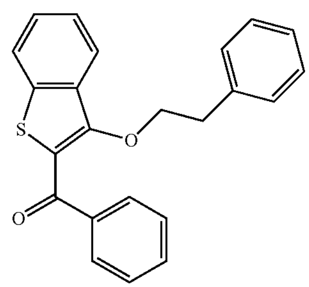 | C$_{23}$H$_{18}$O$_2$S | 358.46 | M + 1 = 359 | 87.7 | 6.13 | |
| 24 | 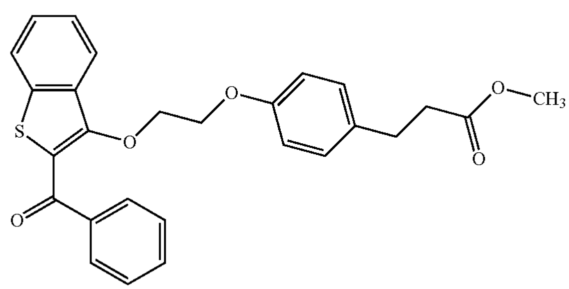 | C$_{27}$H$_{24}$O$_5$S | 460.55 | | | | |
| 25 | 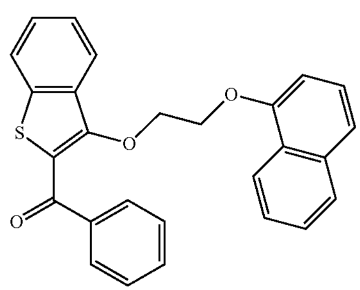 | C$_{27}$H$_{20}$O$_3$S | 424.52 | | | | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 26 | 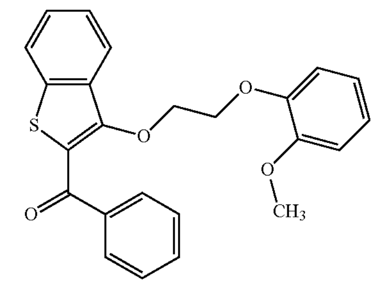 | $C_{24}H_{20}O_4S$ | 404.49 | M + 1 = 405 | 71.7 | 4.05 | |
| 27 | 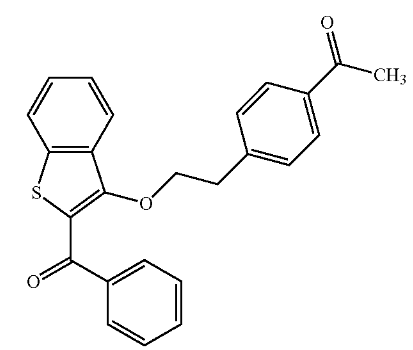 | $C_{25}H_{20}O_3S$ | 400.50 | | | | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 28 | 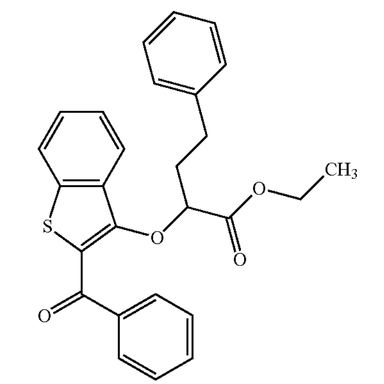 | $C_{27}H_{24}O_4S$ | 444.55 | M + 1 = 445 | 86.4 | 6.11 | |
| 29 | 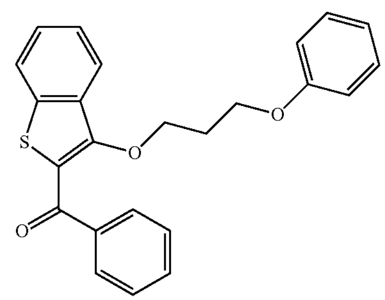 | $C_{24}H_{20}O_3S$ | 388.49 | M + 1 = 389 | 73.4 | 2.55 | |
| 30 | 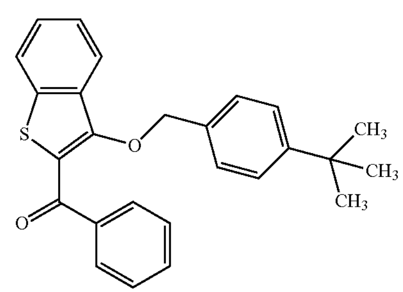 | $C_{26}H_{24}O_2S$ | 400.54 | | 93.4 | 1.26 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 31 | 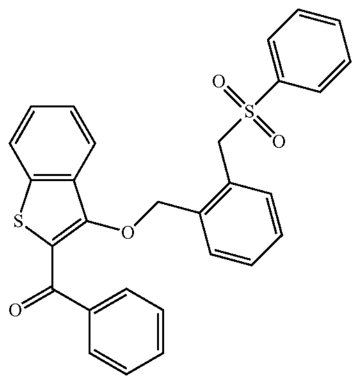 | $C_{29}H_{22}O_4S_2$ | 498.62 | M + 1 = 499 | 81.4 | 3.43 | |
| 32 | 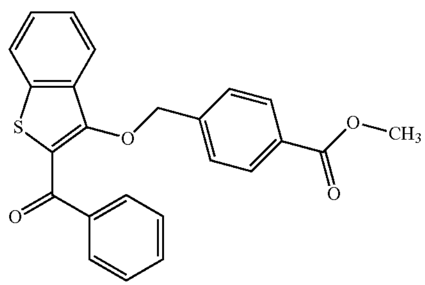 | $C_{24}H_{18}O_4S$ | 402.47 | M + 1 = 403 | 63.1 | 5.24 | |
| 33 | 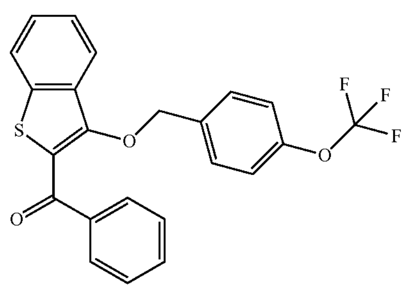 | $C_{23}H_{15}F_3O_3S$ | 428.43 | | 60.6 | 5.18 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 34 | 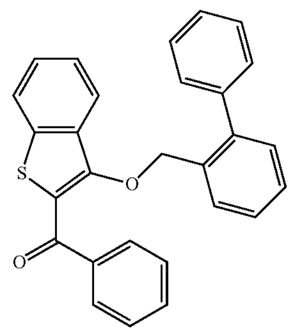 | $C_{28}H_{20}O_2S$ | 420.53 | | 67.1 | 2.92 | |
| 35 | 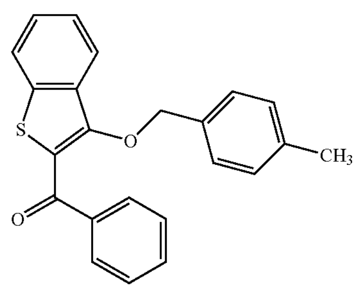 | $C_{23}H_{18}O_2S$ | 358.46 | | 62.7 | 2.92 | |
| 36 | 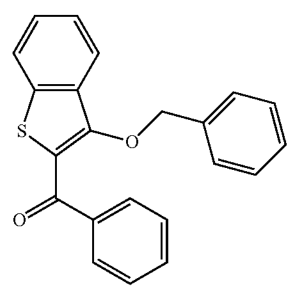 | $C_{22}H_{16}O_2S$ | 344.44 | M + 1 = 345 | 57.3 | 5.45 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 37 | 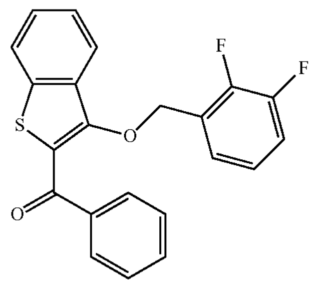 | $C_{22}H_{14}F_2O_2S$ | 380.42 | M + 1 = 381 | | 5.04 | |
| 38 | 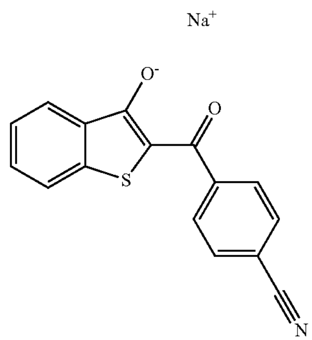 | $C_{16}H_8NNaO_2S$ | 301.30 | 14317 | | | 7.50 (m, 8H) |
| 39 | 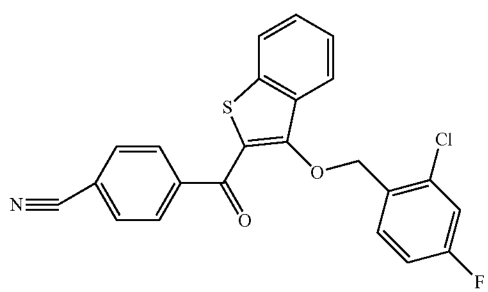 | $C_{23}H_{13}ClFNO_2S$ | 421.88 | M + 1 = 422 | 97.8 | 4.6 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 40 | (3,4-dichlorobenzyl structure) | $C_{23}H_{13}Cl_2NO_2S$ | 438.34 | M + 1 = 438 | 81.1 | 5.64 | 5.08 (s, 2H) 7.11 (m, 2H) 7.57 (m, 2H) 7.90 (m, 5H) |
| 41 | (3-trifluoromethylbenzyl structure) | $C_{24}H_{14}F_3NO_2S$ | 437.44 | M + 1 = 438 | 84.1 | 4.26 | 5.16 (s, 2H) 7.57 (m, 6H) 7.88 (m, 4H) 8.11 (m, 2H) |
| 42 | (2-cyanobenzyl structure) | $C_{24}H_{14}N_2O_2S$ | 394.46 | M + 1 = 395 | 99 | 2.28 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 43 | 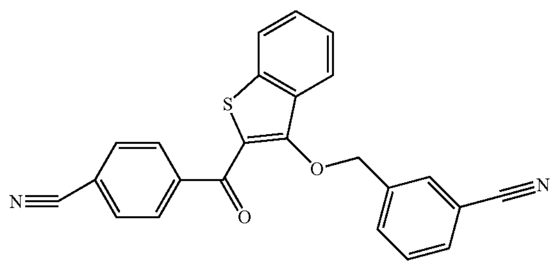 | $C_{24}H_{14}N_2O_2S$ | 394.46 | M + 1 = 395 | 99 | 2.29 | |
| 44 | 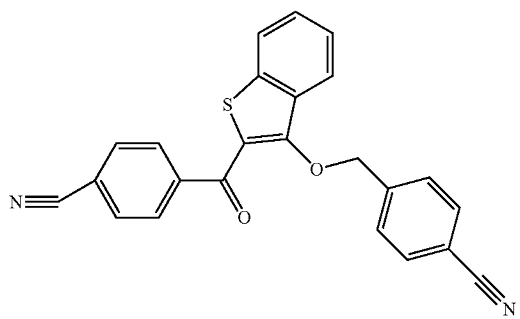 | $C_{24}H_{14}N_2O_2S$ | 394.46 | | | | 5.19 (s, 2H) 7.26 (m, 2H) 7.89 (m, 10H) |
| 45 | 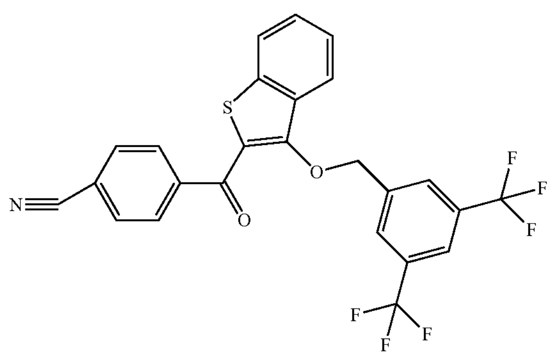 | $C_{25}H_{13}F_6NO_2S$ | 505.44 | | | | 5.41 (s, 2H) 7.94 (m, 11H) |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 46 | 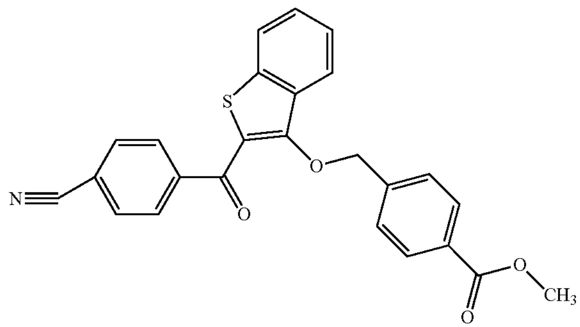 | $C_{25}H_{17}NO_4S$ | 427.48 | M + 1 = 428 | 99 | 3.31 | |
| 47 | 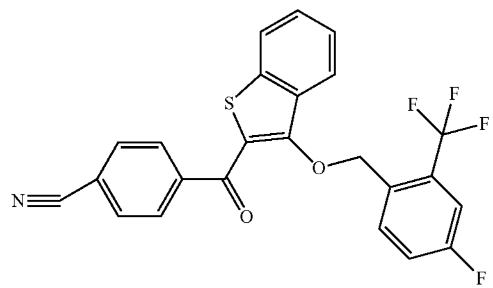 | $C_{24}H_{13}F_4NO_2S$ | 455.43 | | | | 5.22 (s, 2H)<br>7.85 (m, 11H) |
| 48 | 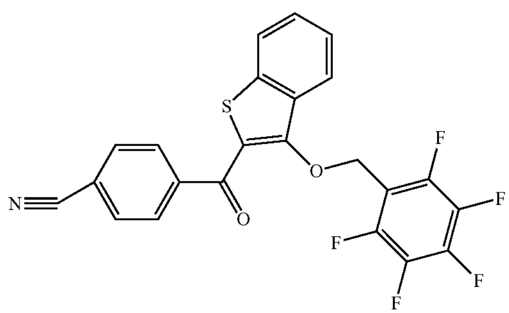 | $C_{23}H_{10}F_5NO_2S$ | 459.40 | | | | 5.40 (s, 2H)<br>8.15 (m, 8H) |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 49 | 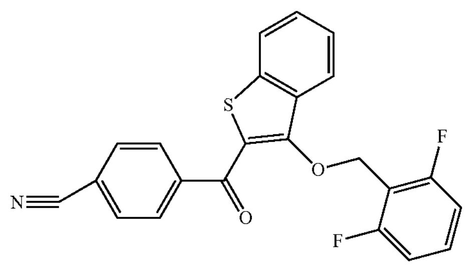 | C$_{23}$H$_{13}$F$_2$NO$_2$S | 405.43 | M + 1 = 406 | 99 | 3.28 | |
| 50 | 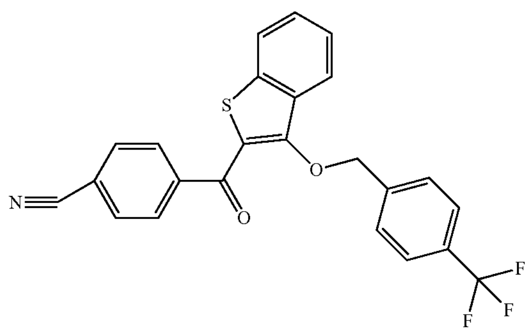 | C$_{24}$H$_{14}$F$_3$NO$_2$S | 437.44 | | | | 5.19 (s, 2H)<br>7.28 (m, 2H)<br>7.88 (m, 10H) |
| 51 | 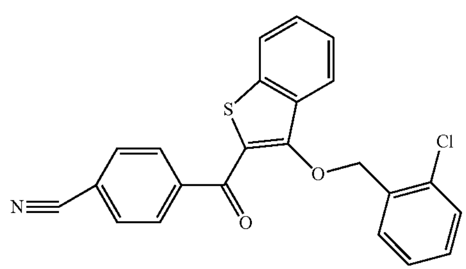 | C$_{23}$H$_{14}$ClNO$_2$S | 403.89 | M + 1 = 404 | 99 | 4.64 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 52 | 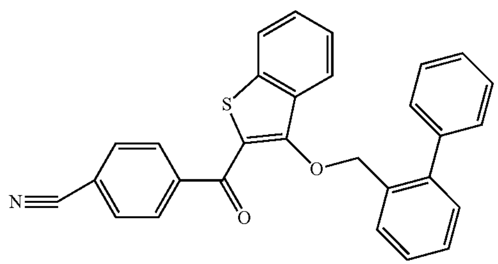 | $C_{29}H_{19}NO_2S$ | 445.54 | M + 1 = 446 | 99 | 7.28 | |
| 53 | 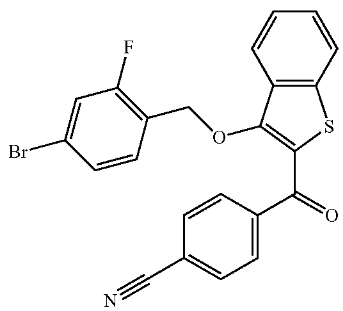 | $C_{23}H_{13}BrFNO_2S$ | 466.33 | M + 1 = 467 | 99 | 5.28 | |
| 54 | 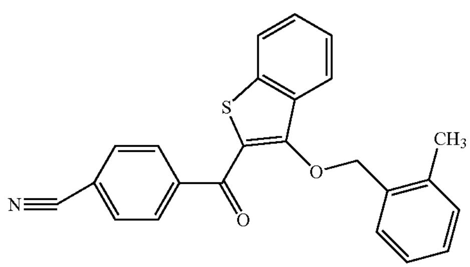 | $C_{24}H_{17}NO_2S$ | 383.47 | M + 1 = 484 | 99 | 4.45 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 55 | 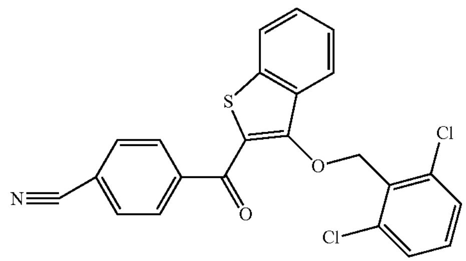 | $C_{23}H_{13}Cl_2NO_2S$ | 438.34 | M + 1 = 439 | 99 | 4.76 | |
| 56 | 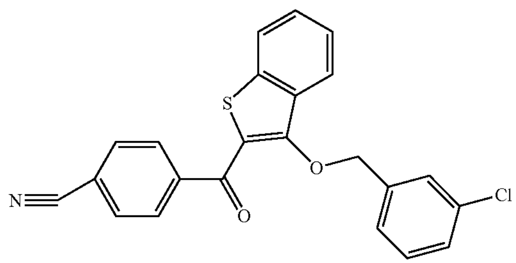 | $C_{23}H_{14}ClNO_2S$ | 403.89 | M + 1 = 404 | 99 | 4.44 | |
| 57 | 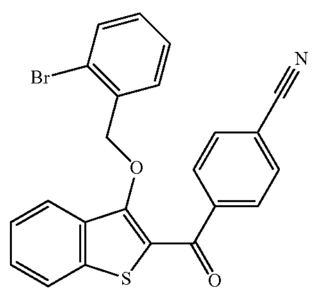 | $C_{23}H_{14}BrNO_2S$ | 448.34 | M + 1 = 449 | 85.5 | 5.02 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 58 | 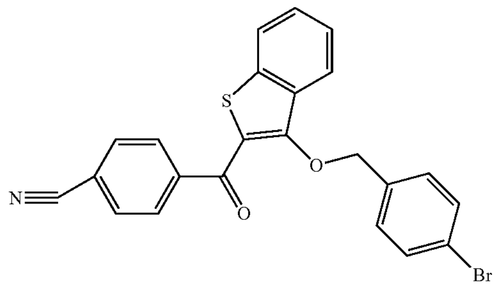 | $C_{23}H_{14}BrNO_2S$ | 448.34 | | 85.6 | 5.02 | |
| 59 | 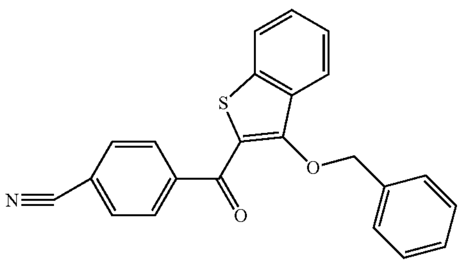 | $C_{23}H_{15}NO_2S$ | 369.45 | | | | 5.02 (s, 2H)<br>6.97 (m, 2H)<br>7.31 (m, 3H)<br>7.55 (m, 2H)<br>7.91 (m, 6H) |
| 60 | 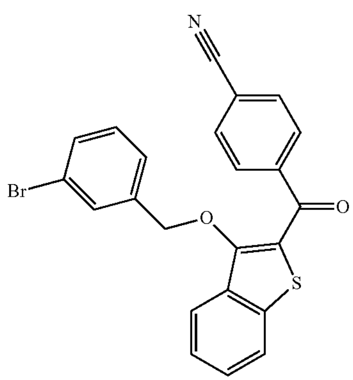 | $C_{23}H_{14}BrNO_2S$ | 448.34 | M + 1 = 449 | 99 | 5.02 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 61 | 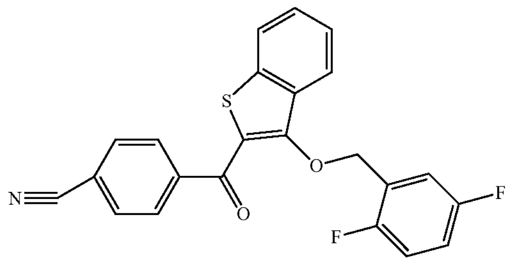 | $C_{23}H_{13}F_2NO_2S$ | 405.43 | M + 1 = 406 | 91.3 | 6.4 | |
| 62 | 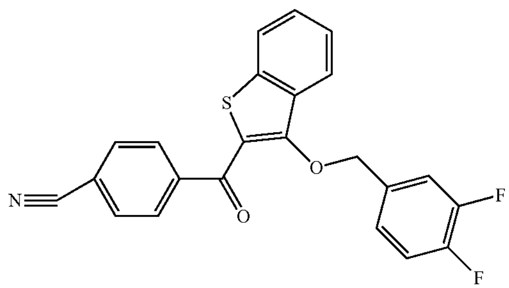 | $C_{23}H_{13}F_2NO_2S$ | 405.43 | M + 1 = 406 | 99.1 | 3.45 | |
| 63 | 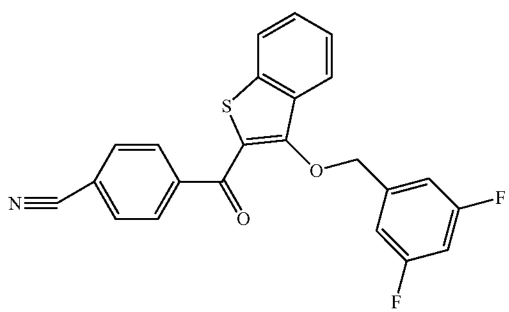 | $C_{23}H_{13}F_2NO_2S$ | 405.43 | M + 1 = 406 | 86.9 | 3.42 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 64 | 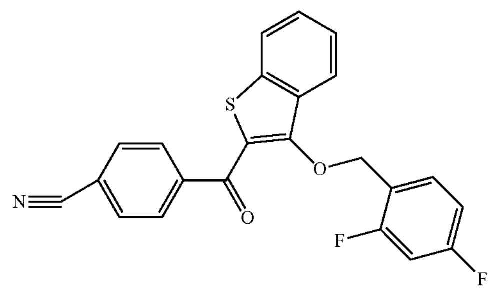 | $C_{23}H_{13}F_2NO_2S$ | 405.43 | M + 1 = 4060 | 99 | 3.45 | |
| 65 | 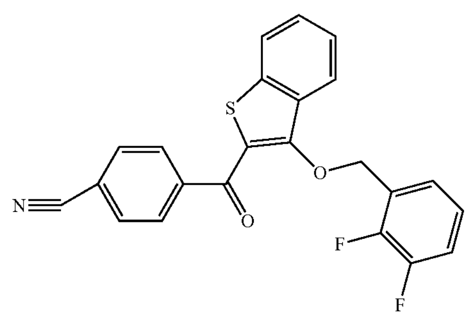 | $C_{23}H_{13}F_2NO_2S$ | 405.43 | M + 1 = 406 | 90.1 | 3.41 | 3.27 (s, 3H) 5.20 (m, 2H) 7.32 (m, 2H) 7.56 (m, 3H) 7.93 (m, 7H) |
| 66 | 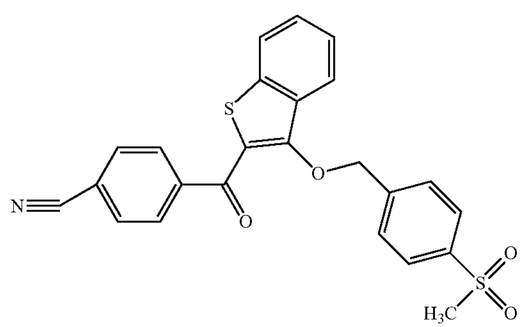 | $C_{24}H_{17}NO_4S_2$ | 447.54 | M + 1 = 448 | | | 4.91 (s, 2H) 6.69 (m, 2H) 7.52 (m, 4H) 7.82 (m, 6H) |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 67 | 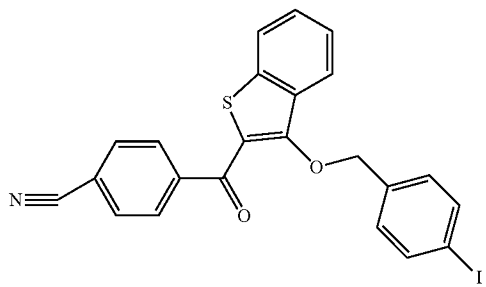 | $C_{23}H_{14}INO_2S$ | 495.34 | | | | |
| 68 | 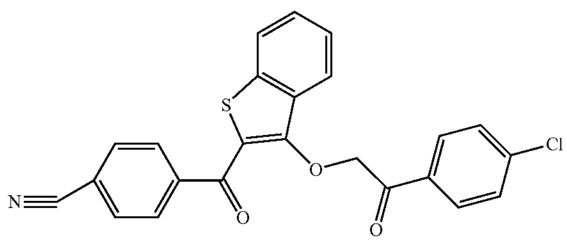 | $C_{24}H_{14}ClNO_3S$ | 431.90 | M + 1 = 432 | 99 | 3.3 | |
| 69 | 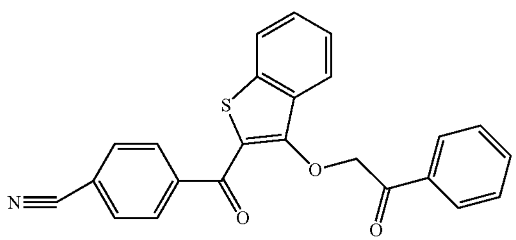 | $C_{24}H_{15}NO_3S$ | 397.46 | M + 1 = 398 | 60.2 | 2.51 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 70 | 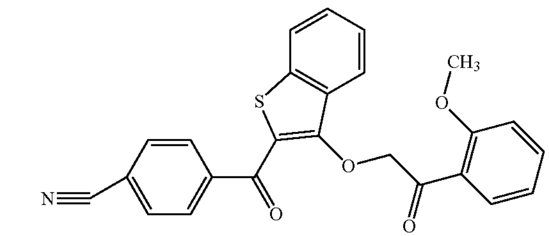 | $C_{25}H_{17}NO_4S$ | 427.48 | M + 1 = 428 | 99 | 2.86 | |
| 71 | 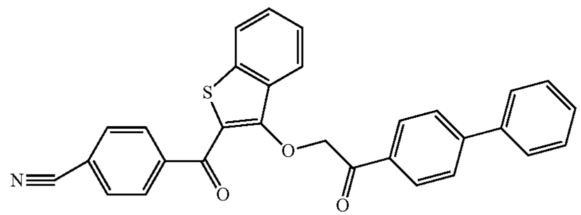 | $C_{30}H_{19}NO_3S$ | 473.55 | M + 1 = 474 | 70.5 | 5.62 | |
| 72 | 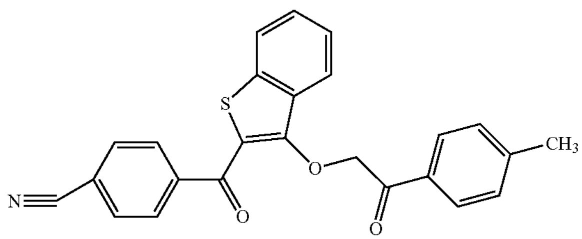 | $C_{25}H_{17}NO_3S$ | 411.48 | M + 1 = 412 | 79 | 3.03 | |
| 73 | 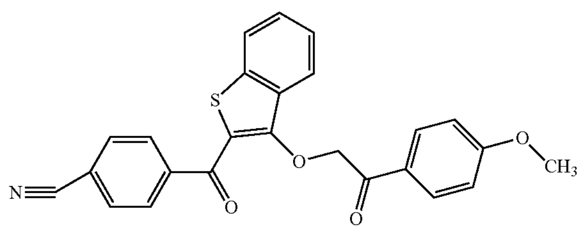 | $C_{25}H_{17}NO_4S$ | 427.48 | M + 1 = 428 | 59.7 | 2.54 | |

TABLE A-continued
Hewlett Packard LC/MSD (Simple Quad)-Orthogonal Spray Source APCI, HP Series 1100 line with diode array
| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 74 | 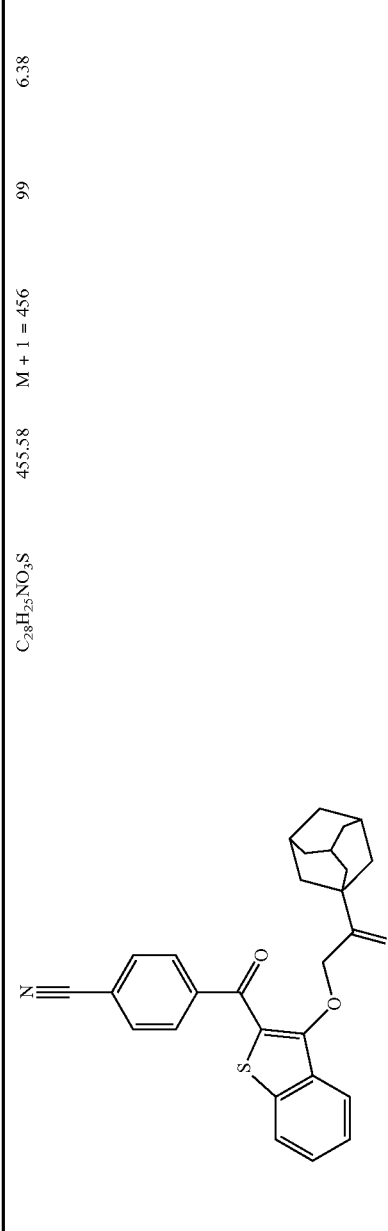 | $C_{28}H_{25}NO_3S$ | 455.58 | M + 1 = 456 | 99 | 6.38 | |
| 75 | 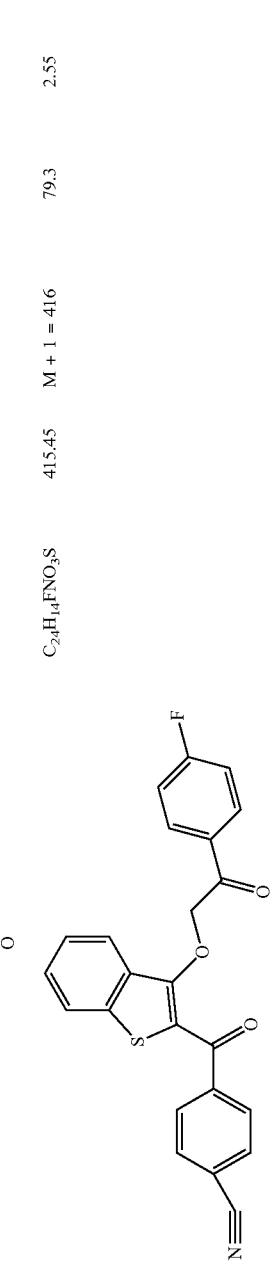 | $C_{24}H_{14}FNO_3S$ | 415.45 | M + 1 = 416 | 79.3 | 2.55 | |
| 76 | 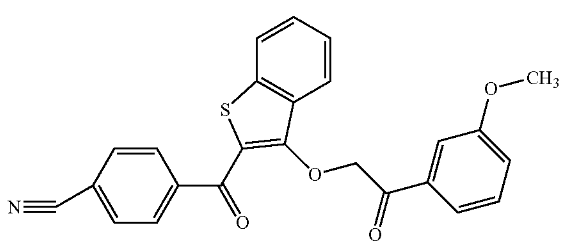 | $C_{25}H_{17}NO_4S$ | 427.48 | M + 1 = 428 | 71.3 | 2.74 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 77 | 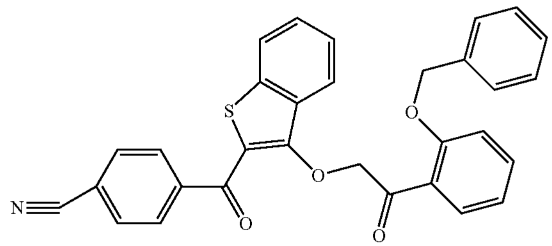 | C$_{31}$H$_{21}$NO$_4$S | 503.58 | M + 1 = 504 | 99 | 4.74 | |
| 78 | 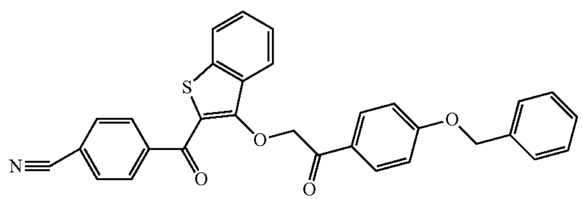 | C$_{31}$H$_{21}$NO$_4$S | 503.58 | M + 1 = 504 | 77.2 | 5.26 | |
| 79 | 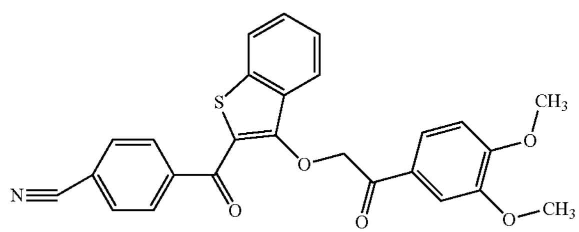 | C$_{26}$H$_{19}$NO$_5$S | 457.51 | M + 1 = 504 | 99 | 2.15 | |
| 80 | 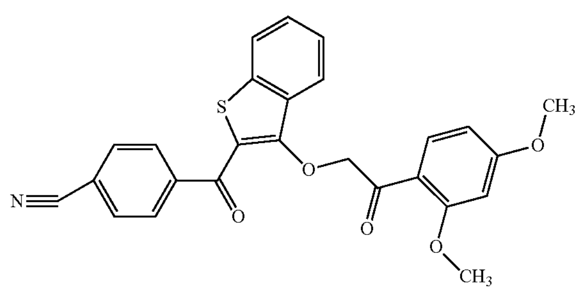 | C$_{26}$H$_{19}$NO$_5$S | 457.51 | M + 1 = 458 | 76.8 | 1.77 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 81 | 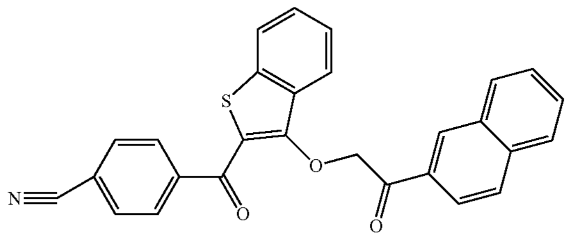 | $C_{28}H_{17}NO_3S$ | 447.52 | M + 1 = 448 | 69.1 | 1.96 | |
| 82 | 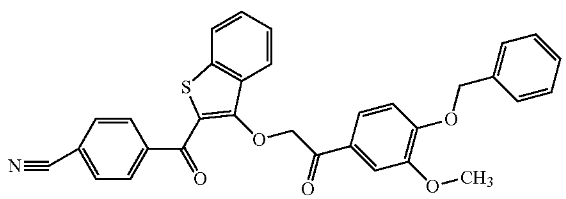 | $C_{32}H_{23}NO_5S$ | 533.61 | M + 1 = 534 | 43.2 | 1.89 | |
| 83 | 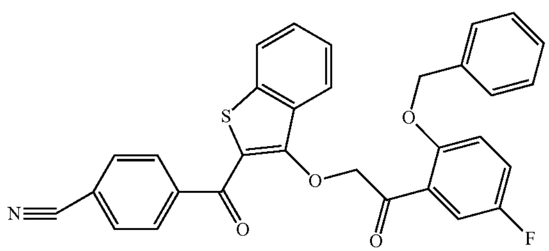 | $C_{31}H_{20}FNO_4S$ | 521.57 | M + 1 = 522 | 99 | 5.05 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 84 | 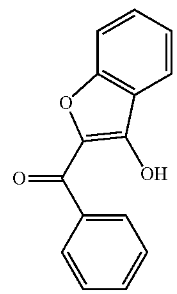 | C$_{15}$H$_{10}$O$_3$ | 238.25 | 14377 | | | 7.50 (s, 1H)<br>7.58 (m, 1H)<br>7.91 (m, 5H)<br>8.30 (m, 3H) |
| 85 | 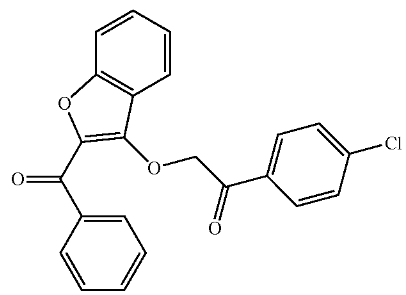 | C$_{23}$H$_{15}$ClO$_4$ | 390.83 | M + 1 = 391 | 99 | 4.31 | |
| 86 | 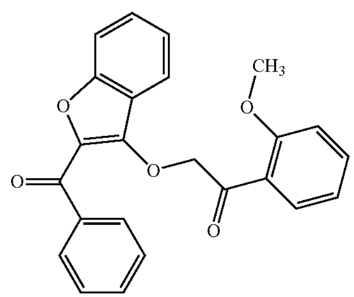 | C$_{24}$H$_{18}$O$_5$ | 386.41 | M + 1 = 387 | 99 | 3.08 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 87 | 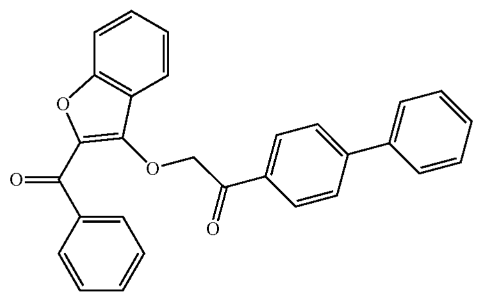 | $C_{29}H_{20}O_4$ | 432.48 | | | | |
| 88 | 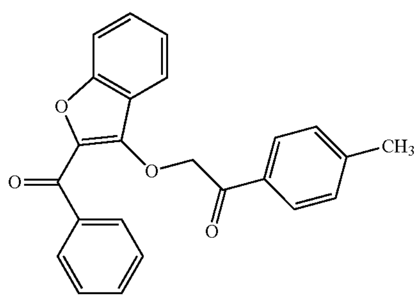 | $C_{24}H_{18}O_4$ | 370.41 | M + 1 = 371 | 99 | 3.6 | |
| 89 | 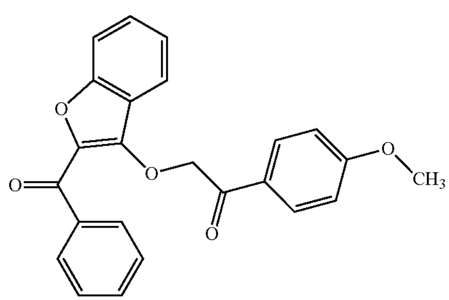 | $C_{24}H_{18}O_5$ | 386.41 | M + 1 = 387 | 99 | 2.9 | |

TABLE A-continued

Hewlett Packard LC/MSD (Simple Quad)-Orthogonal Spray Source APCI, HP Series 1100 line with diode array

| Products | Structure | Formula | Mol. weight g.mol$^{-1}$ | MS | Purity (%) | Tr (min) | 1H NMR 200 MHz DMSOd6 (δ ppm) |
|---|---|---|---|---|---|---|---|
| 90 | 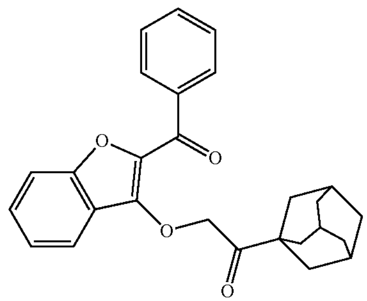 | C$_{27}$H$_{26}$O$_4$ | 414.51 | M + 1 = 415.1 | 84.7 | 7.05 | |
| 91 | 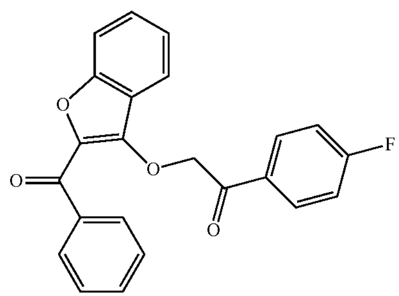 | C$_{23}$H$_{15}$FO$_4$ | 374.37 | M + 1 = 375.1 | 99 | 2.96 | |
| 92 | 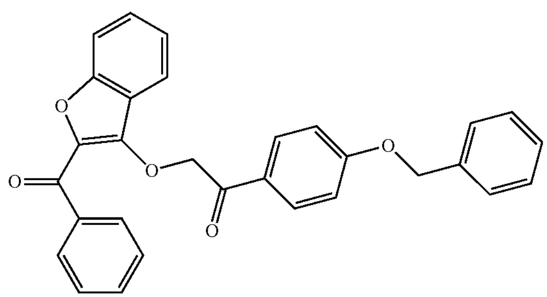 | C$_{30}$H$_{22}$O$_5$ | 462.51 | M + 1 = 463.1 | 85 | 6.22 | |

TABLE A-continued

Hewlett Packard LC/MSD (Simple Quad)-Orthogonal Spray Source APCI, HP Series 1100 line with diode array

| Products | Structure | Formula | Mol. weight g.mol⁻¹ | MS | Purity (%) | Tr (min) | 1H NMR 200 MHz DMSOd6 (δ ppm) |
|---|---|---|---|---|---|---|---|
| 93 | 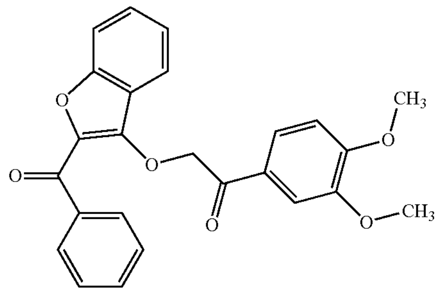 | $C_{25}H_{20}O_6$ | 416.43 | | | | |
| 94 | 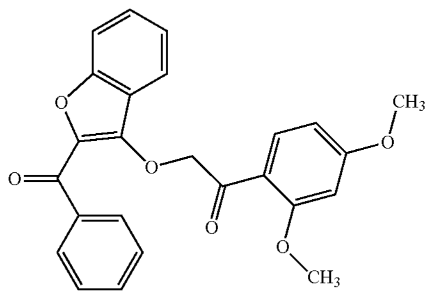 | $C_{25}H_{20}O_6$ | 416.43 | M + 1 = 417.1 | 99 | 3.09 | |
| 95 | 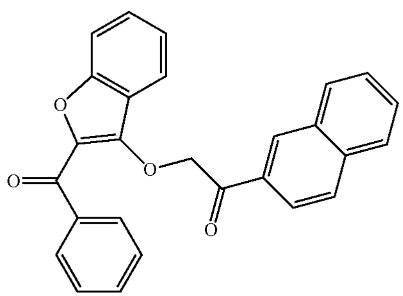 | $C_{27}H_{18}O_4$ | 406.44 | M + 1 = 407.1 | 99 | 5.18 | |

By way of example, the following compounds were prepared according to the procedures described above:
(2-benzoylbenzo[b]thiophen-3-yloxy)acetic acid
[2-(4-chlorobenzoyl)benzo[b]thiophen-3-yloxy]acetic acid
[2-(2,2-dimethylpropionyl)benzo[b]thiophen-3-yloxy]acetic acid
4-(2-benzoylbenzo[b]thiophen-3-yloxy)butyric acid
4-[2-(4-chlorobenzoyl)benzo[b]thiophen-3-yloxy]butyric acid
4-[2-(2,2-dimethylpropionyl)benzo[b]thiophen-3-yloxy]butyric acid
5-(2-benzoylbenzo[b]thiophen-3-yloxy)pentanoic acid
5-[2-(4-chlorobenzoyl)benzo[b]thiophen-3-yloxy]pentanoic acid
5-[2-(2,2-dimethylpropionyl)benzo[b]thiophen-3-yloxy]pentanoic acid
6-(2-benzoylbenzo[b]thiophen-3-yloxy)hexanoic acid
6-[2-(4-chlorobenzoyl)benzo[b]thiophen-3-yloxy]hexanoic acid
6-[2-(2,2-dimethylpropionyl)benzo[b]thiophen-3-yloxy]hexanoic acid
2-(2-benzoylbenzo[b]thiophen-3-yloxy)-3-methoxypropionic acid
3-{4-[2-(2-benzoylbenzo[b]thiophen-3-yloxy)ethoxy]phenyl}propionic acid
3-(4-{2-[2-(2,2-dimethylpropionyl)benzo[b]thiophen-3-yloxy]ethoxy}phenyl)propionic acid
2-[2-(4-chlorobenzoyl)benzo[b]thiophen-3-yloxy]butyric acid
2-[2-(2,2-dimethylpropionyl)benzo[b]thiophen-3-yloxy]butyric acid
2-(2-benzoylbenzo[b]thiophen-3-yloxy)pentanoic acid
2-[2-(4-chlorobenzoyl)benzo[b]thiophen-3-yloxy]pentanoic acid
2-[2-(2,2-dimethylpropionyl)benzo[b]thiophen-3-yloxy]pentanoic acid
(4-{2-[2-(2,2-dimethyl propionyl)benzo[b]thiophen-3-yloxy]ethoxy}phenyl)acetic acid
4-[2-(2-benzoylbenzo[b]thiophen-3-yloxy)ethoxy]benzoic acid
4-{2-[2-(2,2-dimethylpropionyl)benzo[b]thiophen-3-yloxy]ethoxy}benzoic acid
3-(2-benzoylbenzo[b]thiophen-3-yloxymethyl)benzoic acid
3-[2-(4-chlorobenzoyl)benzo[b]thiophen-3-yloxymethyl]benzoic acid
4-[2-(4-chlorobenzoyl)benzo[b]thiophen-3-yloxymethyl]benzoic acid
2-(2-benzoylbenzo[b]thiophen-3-yloxy)butyric acid
1-[2-(2,2-dimethylpropionyl)benzo[b]thiophen-3-yloxy]-3,3-dimethylbutan-2-one
1-[2-(4-chlorobenzoyl)benzo[b]thiophen-3-yloxy]-3,3-dimethylbutan-2-one
1-[2-(4-fluorobenzoyl)benzo[b]thiophen-3-yloxy]-3,3-dimethylbutan-2-one
1-(2-benzoyl-5-fluorobenzo[b]thiophen-3-yloxy)-3,3-dimethylbutan-2-one
1-[5-fluoro-2-(4-methoxybenzoyl)benzo[b]thiophen-3-yloxy]-3,3-dimethylbutan-2-one
1-[5-fluoro-2-(4-fluorobenzoyl)benzo[b]thiophen-3-yloxy]-3,3-dimethyl butan-2-one
1-[2-(4-methoxybenzoyl)benzo[b]thiophen-3-yloxy]-3,3-dimethylbutan-2-one
4-[2-(4-fluorobenzoyl)benzo[b]thiophen-3-yloxy]butyric acid
5-[2-(4-fluorobenzoyl)benzo[b]thiophen-3-yloxy]pentanoic acid
6-[2-(4-fluorobenzoyl)benzo[b]thiophen-3-yloxy]hexanoic acid
2-[2-(4-fluorobenzoyl)benzo[b]thiophen-3-yloxy]-3-methoxypropionic acid
2-[2-(4-fluorobenzoyl)benzo[b]thiophen-3-yloxy]butyric acid
2-[2-(4-fluorobenzoyl)benzo[b]thiophen-3-yloxy]pentanoic acid
4-[2-(4-fluorobenzoyl)benzo[b]thiophen-3-yloxymethyl]benzoic acid
(2-acetylbenzo[b]thiophen-3-yloxy)acetic acid
5-(2-acetylbenzo[b]thiophen-3-yloxy)pentanoic acid
6-(2-acetylbenzo[b]thiophen-3-yloxy)hexanoic acid
2-(2-acetylbenzo[b]thiophen-3-yloxy)-3-methoxypropionic acid
3-{4-[2-(2-acetylbenzo[b]thiophen-3-yloxy)ethoxy]phenyl}propionic acid
2-(2-acetylbenzo[b]thiophen-3-yloxy)-4-phenyl butyric acid
2-(2-acetylbenzo[b]thiophen-3-yloxy)butyric acid
2-(2-acetylbenzo[b]thiophen-3-yloxy)pentanoic acid
{4-[2-(2-acetylbenzo[b]thiophen-3-yloxy)ethoxy]phenyl}acetic acid
[2-(4-fluorobenzoyl)benzo[b]thiophen-3-yloxy]acetic acid

II.—BIOLOGICAL RESULTS

Test of Insulin Secretion According to the Method Described in *Endocrinology*, 1992 vol. 130 (1) pp. 167-178

The insulin-secreting activities are collated in Table B. The compounds according to the invention were tested at a concentration of $10^{-5}$ M.

TABLE B

Sec INS corresponds to the % of insulin secretion.

| Products | SEC INS1 |
|---|---|
| 1 | 206% |
| 3 | 244% |
| 8 | 193% |
| 14 | 287% |
| 15 | 207% |
| 42 | 283% |
| 43 | 257% |
| 55 | 174% |
| 59 | 229% |
| 66 | 202% |
| 69 | 179% |
| 70 | 189% |
| 72 | 185% |
| 86 | 164% |

Study of the Activity on Isolated Rat Islets

Effect of the chemical compounds on insulin secretion as a function of the glucose concentration, in vitro, in isolated islets of Langerhans in static incubation (Table C):

The islets of Langerhans obtained by digestion of exocrine pancreatic tissue with collagenase, and then purified on Ficoll gradient, are incubated for 90 minutes in the presence of two concentrations of glucose, (2.8 mM or 8 mM), in the presence or absence of the chemical compound. The insulin secretion is assayed by RIA in the incubation medium.

The potential of the various chemical compounds to stimulate insulin secretion is estimated by calculating the stimulation factor*.

A compound stimulates the secretion of insulin if this factor is greater than or equal to 130% for a given dose of glucose.

$$*NB: \text{Stimulation factor} = \frac{(G + \text{product}) * 100}{G}$$

where:

G=secretion of insulin (pmol/min. islet) in the presence of glucose alone

G+product=secretion of insulin (pmol/min. islet) in the presence of the same concentration of glucose and of the test chemical compound.

TABLE C

| | | Insulin secretion stimulation factor. | |
|---|---|---|---|
| | | Insulin secretion stimulation factor | |
| Product | Dose | Product + G2.8 mM | Product + G8 mM |
| 1 | $10^{-5}$ M | 98% | 135% |
| 15 | $10^{-6}$ M | 125% | 183% |
| | $10^{-5}$ M | 119% | 152% |
| 43 | $10^{-5}$ M | 108% | 135% |

The compounds according to the invention are thus insulin-secretory in response to glucose. They thus make it possible to avoid the risk of hypoglycaemia; this is in contrast with simple hypoglycaemiant compounds, the hypoglycaemiant effect of which is independent of the concentration of glucose in the body.

Study of the Antidiabetic Activity in NOSTZ rats

Effect/Dose of compound 15, in vivo, in the case of NOSTZ diabetic rats (Table D):

NOSTZ rats, made diabetic by injection of steptozotocin on the day of birth (Portha et al.; 1974), are treated, orally, daily by administration of 50-100-200 mg/kg of body weight of compound 15, of 200 mg/kg of metformin (reference anti-diabetic agent) or of methylcellulose (controls). Blood samples are taken from the anaesthetized animal two hours after the fourth treatment. The glycaemia is measured via the colorimetric method using glucose dehydrogenase.

TABLE D

| Effect on glycaemia of the administration of a daily dose repeated for 4 days of compound 15 (50 - 100 - 200 mg/kg/day) or of metformin 200 mg/kg/day, in NOSTZ diabetic rats. | |
|---|---|
| Treatment | Percentage of variation of glycaemia relative to the controls |
| Reference: metformin 200 mg/kg/day | −29%** |
| Compound 15 - 50 mg/kg/day | −13%* |
| Compound 15 - 100 mg/kg/day | −23%** |
| Compound 15 - 200 mg/kg/day | −18%** |

% of variation of glycaemia relative to the controls for 5 or 6 observations.
*$p \leq 0.05$;
**$p \leq 0.01$, relative to the value of the N0STZ controls (analysis covariance test F).

The antidiabetic activity of the compounds of the formula (I) orally was determined on an experimental model of non-insulin-dependent diabetes, induced in rats with steptozotocin.

The model of non-insulin-dependent diabetes is obtained in the rats by means of a neonatal injection of steptozotocin.

The diabetic rats used are eight weeks old. The animals are housed, from the day of birth to the day of the experiment, in an animal house at a regulated temperature of 21 to 22° C. and subjected to a fixed cycle of light (from 7 a.m. to 7 p.m.) and darkness (from 7 p.m. to 7 a.m.). Their food consisted of a maintenance diet, and water and food were given "ad libitum", with the exception of fasting two hours before the tests, during which period the food is removed (post-absorptive state).

The rats are treated orally for one (D1) or four (D4) days with the test product.

Two hours after the final administration of the product and 30 minutes after anaesthetizing the animals with pentobarbital sodium (Nembutal®), a 300 μl blood sample is taken from the end of the tail.

By way of example, the results obtained are collated in Table D.

These results show the efficacy of the compounds of the formula (I) in reducing glycaemia in the case of diabetic animals. These results are expressed as a percentage change in the glycaemia on D1 and D4 (number of days of treatment) relative to D0 (before the treatment).

The invention claimed is:

1. Compounds of the general formula (I):

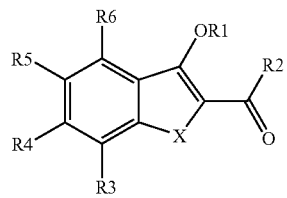

in which:
X=O or S;
R1 is chosen from:
Alk-COOH,
Alk-C(=O)—(O)$_m$—Ar,
Alk-C(=O)—(O)$_m$-Het,
Alk-C(=O)—(O)$_m$-Alk,
Alk-C(=O)—(O)$_m$-cycloalkyl,
Alk-C(=O)NRR',
Alk-(O)$_m$—Ar,
Alk-O-Alk,
Alk-O-Alk-Ar,
Alk-O-Het,
R2 is chosen from -Alk, —Ar and -cycloalkyl;
R3, R4, R5 and R6, which may be identical or different, are chosen independently from H, -Hal, —OH, -Alk, —OAlk, —CN, —CF$_3$, —NRR' and —NO$_2$;
in which, in the definitions of R1-R6:
each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;
each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;

R and R' are chosen independently from H and Alk;

m=0 or 1;

and also the stereoisomers thereof, the racemates thereof and the pharmaceutically acceptable salts, with the exception of the compounds for which:

1) R1=—CH$_2$—C(=O)Me, R2=-Me, X=O, R3, R5=H and each R4, R6=H or OMe.

2. Compounds of the formula (I) according to claim 1, in which:

X=O or S;

R1 is chosen from:
  Alk-COOH,
  Alk-C(=O)—(O)$_m$—Ar,
  Alk-C(=O)—(O)$_m$-Het,
  Alk-C(=O)—(O)$_m$-Alk,
  Alk-C(=O)—(O)$_m$-cycloalkyl,
  Alk-C(=O)NRR',
  Alk-(O)$_m$—Ar,
  Alk-O-Alk,
  Alk-O-Alk-Ar,
  Alk-O-Het, R2 represents —Ar or -cycloalkyl;

R3, R4, R5 and R6, which may be identical or different, are chosen independently from H, -Hal, —OH, -Alk, —OAlk, —CN, —CF$_3$, —NRR' and —NO$_2$;

in which, in the definitions of R1-R6:

each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;

each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;

R and R' are chosen independently from H and Alk;

m=0 or 1, and also the stereoisomers thereof, the racemates thereof and the pharmaceutically acceptable salts.

3. Compounds of the formula (I) according to claim 1, in which:

X=S;

R1 is chosen from:
  Alk-COOH,
  Alk-C(=O)—(O)$_m$—Ar,
  Alk-C(=O)—(O)$_m$-Het,
  Alk-C(=O)—(O)$_m$-Alk,
  Alk-C(=O)—(O)$_m$-cycloalkyl,
  Alk-C(=O)NRR',
  Alk-(O)$_m$—Ar,
  Alk-O-Alk,
  Alk-O-Alk-Ar,
  Alk-O-Het, R2 is chosen from -Alk, —Ar and -cycloalkyl;

R3, R4, R5 and R6, which may be identical or different, are chosen independently from H, -Hal, —OH, -Alk, —OAlk, —CN, —CF$_3$, —NRR' and —NO$_2$;

in which, in the definitions of R1-R6:

each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;

each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;

R and R' are chosen independently from H and Alk;

m=0 or 1;

and also the stereoisomers thereof, the racemates thereof and the pharmaceutically acceptable salts.

4. Compounds of the formula (I) according to claim 1, in which R3, R4, R5, R6=H.

5. Compounds of the formula (I) according to claim 1, in which X=S.

6. Compounds of the formula (I) according to claim 1, in which R2=Ar optionally substituted by —CN or —COOH, or alkyl optionally substituted by —COOH.

7. Compounds of the formula (I) according to claim 1, in which R2=phenyl optionally substituted by —CN or —COOH.

8. Compounds of the formula (I) according to claim 1, in which R2=phenyl substituted by —CN.

9. Compounds of the formula (I) according to claim 1, in which m=0.

10. Compounds of the formula (I) according to claim 1, in which R1=—CH$_2$—COOH, —CH$_2$—C(=O)—(O)$_m$—Ar, —CH$_2$—C(=O)—(O)$_m$-Het, —CH$_2$—C(=O)—(O)$_m$-Alk, —CH$_2$—C(=O)NRR', —CH$_2$—(O)$_m$—Ar, —CH$_2$—O-Alk, —CH$_2$—O-Het, in which Ar is optionally substituted by one or more groups chosen from Hal, —OAlk, —Ar, -Alk, —O-Alk-Ar,—C(=O)—(O)$_m$-Alk, -Alk-C(=O)—(O)$_m$Alk, —S(O)$_n$—Ar, —S(O)$_n$-Alk, —O—CF$_3$ —CN and —OH, in which m=0 or 1, n=2.

11. Compounds of the formula (I) according to claim 1, in which R1=—CH$_2$—C(=O)—Ar, —CH$_2$—C(=O)-Alk or —(CH$_2$)$_m'$—(O)$_m$—Ar, in which Ar is optionally substituted by one or more groups chosen from Hal, —OAlk, —Ar, -Alk, OAlk-Ar, —C(=O)—(O)$_m$-Alk, -Alk-C(=O)—(O)$_n$-Alk, —S(O)$_m$—Ar, —S(O)$_m$-Alk, —O—CF$_3$, —CN and —OH, in which m=0 or 1, m'=1 or 2, n=2.

12. Compounds of the formula (I) according to claim 1, in which m'=2 if m =1.

13. Compounds of the formula (I) according to claim 1, in which R1=—CH$_2$—C(=O)-Alk.

14. Compounds of the formula (I) according to claim 13, in which Alk=-CMe$_3$.

15. Compounds of the formula (I) according to claim 1, in which Ar=phenyl.

16. Compounds of the formula (I) according to claim 1, in which R1=—CH$_2$—C(=O)-phenyl or —CH$_2$-phenyl in which phenyl is optionally substituted by one or more groups chosen from -Hal, —OAlk, —CN, —SO$_2$-Alk and -Alk.

17. Compounds of the formula (I) according to claim 1, chosen from:

2-(2-benzoylbenzo[b]thiophen-3-yloxy)-1-(4-chlorophenyl)ethanone;

2-(2-benzoylbenzo[b]thiophen-3-yloxy)-1-phenylethanone;

2-(2-benzoylbenzo[b]thiophen-3-yloxy)-1-(2-methoxyphenyl)ethanone;

2-(2-benzoylbenzo[b]thiophen-3-yloxy)-1-biphenyl-4-ylethanone;
2-(2-benzoylbenzo[b]thiophen-3-yloxy)-1-p-tolylethanone;
2-(2-benzoylbenzo[b]thiophen-3-yloxy)-1-(4-methoxyphenyl)ethanone;
2-(2-benzoylbenzo[b]thiophen-3-yloxy)-1-(4-fluorophenyl)ethanone;
2-(2-benzoylbenzo[b]thiophen-3-yloxy)-1-(3-methoxyphenyl)ethanone;
methyl 2-(2-benzoylbenzo[b]thiophen-3-yloxy)-3-methoxypropionate;
2-(2-benzoylbenzo[b]thiophen-3-yloxy)-1-(2-benzyloxyphenyl)ethanone;
2-(2-benzoylbenzo[b]thiophen-3-yloxy)-1-(4-benzyloxyphenyl)ethanone;
2-(2-benzoylbenzo[b]thiophen-3-yloxy)-1-(3,4-dimethoxyphenyl)ethanone;
2-(2-benzoylbenzo[b]thiophen-3-yloxy)-1-phenylpropan-1-one;
2-(2-benzoylbenzo[b]thiophen-3-yloxy)-1-(2,4-dimethoxyphenyl)ethanone;
1-(2-benzoylbenzo[b]thiophen-3-yloxy)-3,3-dimethylbutan-2-one;
2-(2-benzoylbenzo[b]thiophen-3-yloxy)-1-naphthalen-2-ylethanone;
2-(2-benzoylbenzo[b]thiophen-3-yloxy)-1-(2,3-dichloro-4-methoxyphenyl)ethanone;
2-(2-benzoylbenzo[b]thiophen-3-yloxy)-1-(4-benzyloxy-3-methoxyphenyl)ethanone;
2-(2-benzoylbenzo[b]thiophen-3-yloxy)-1-(2-benzyloxy-5-fluorophenyl)ethanone;
(3-hydroxybenzo[b]thiophen-2-yl)phenylmethanone;
2-(2-benzoylbenzo[b]thiophen-3-yloxy)acetamide;
{3-[2-(4-fluorophenoxy)ethoxy]benzo[b]thiophen-2-yl}phenylmethanone;
(3-phenethyloxybenzo[b]thiophen-2-yl)phenylmethanone;
methyl 3-{4-[2-(2-benzoylbenzo[b]thiophen-3-yloxy)ethoxy]phenyl}propionate;
{3-[2-(naphthalen-1-yloxy)ethoxy]benzo[b]thiophen-2-yl}phenylmethanone;
{3-[2-(2-methoxyphenoxy)ethoxy]benzo[b]thiophen-2-yl}phenylmethanone;
1-{4-[2-(2-benzoylbenzo[b]thiophen-3-yloxy)ethyl]phenyl}ethanone;
ethyl 2-(2-benzoylbenzo[b]thiophen-3-yloxy)-4-phenylbutyrate;
[3-(3-phenoxypropoxy)benzo[b]thiophen-2-yl]phenylmethanone;
[3-(4-tert-butylbenzyloxy)benzo[b]thiophen-2-yl]phenylmethanone;
[3-(2-benzenesulfonylmethylbenzyloxy)benzo[b]thiophen-2-yl]phenylmethanone;
methyl 4-(2-benzoylbenzo[b]thiophen-3-yloxymethyl)benzoate;
phenyl[3-(4-trifluoromethoxybenzyloxy)benzo[b]thiophen-2-yl]methanone;
[3-(biphenyl-2-ylmethoxy)benzo[b]thiophen-2-yl]phenylmethanone;
[3-(4-methylbenzyloxy)benzo[b]thiophen-2-yl]phenylmethanone;
(3-benzyloxybenzo[b]thiophen-2-yl)phenylmethanone;
[3-(2,3-difluorobenzyloxy)benzo[b]thiophen-2-yl]phenylmethanone;
sodium 2-(4-cyanobenzoyl)benzo[b]thiophen-3-olate;
4-[3-(2-chloro-4-fluorobenzyloxy)benzo[b]thiophene-2-carbonyl]benzonitrile;
4-[3-(3,4-dichlorobenzyloxy)benzo[b]thiophene-2-carbonyl]benzonitrile;
4-[3-(3-trifluoromethylbenzyloxy)benzo[b]thiophene-2-carbonyl]benzonitrile;
4-[3-(2-cyanobenzyloxy)benzo[b]thiophene-2-carbonyl]benzonitrile;
4-[3-(3-cyanobenzyloxy)benzo[b]thiophene-2-carbonyl]benzonitrile;
4-[3-(4-cyanobenzyloxy)benzo[b]thiophene-2-carbonyl]benzonitrile;
4-[3-(3,5-bis-trifluoromethylbenzyloxy)benzo[b]thiophene-2-carbonyl]benzonitrile;
methyl 4-[2-(4-cyanobenzoyl)benzo[b]thiophen-3-yloxymethyl]benzoate;
4-[3-(4-fluoro-2-trifluoromethylbenzyloxy)benzo[b]thiophene-2-carbonyl]benzonitrile;
4-(3-pentafluorophenylmethoxybenzo[b]thiophene-2-carbonyl)benzonitrile;
4-[3-(2,6-difluorobenzyloxy)benzo[b]thiophene-2-carbonyl]benzonitrile;
4-[3-(4-trifluoromethylbenzyloxy)benzo[b]thiophene-2-carbonyl]benzonitrile;
4-[3-(2-chlorobenzyloxy)benzo[b]thiophene-2-carbonyl]benzonitrile;
4-[3-(biphenyl-2-ylmethoxy)benzo[b]thiophene-2-carbonyl]benzonitrile;
4-[3-(4-bromo-2-fluorobenzyloxy)benzo[b]thiophene-2-carbonyl]benzonitrile;
4-[3-(2-methylbenzyloxy)benzo[b]thiophene-2-carbonyl]benzonitrile;
4-[3-(2,6-dichlorobenzyloxy)benzo[b]thiophene-2-carbonyl]benzonitrile;
4-[3-(3-chlorobenzyloxy)benzo[b]thiophene-2-carbonyl]benzonitrile;
4-[3-(2-bromobenzyloxy)benzo[b]thiophene-2-carbonyl]benzonitrile;
4-[3-(4-bromobenzyloxy)benzo[b]thiophene-2-carbonyl]benzonitrile;
4-(3-benzyloxybenzo[b]thiophene-2-carbonyl)benzonitrile;
4-[3-(3-bromobenzyloxy)benzo[b]thiophene-2-carbonyl]benzonitrile;
4-[3-(2,5-difluorobenzyloxy)benzo[b]thiophene-2-carbonyl]benzonitrile;
4-[3-(3,4-difluorobenzyloxy)benzo[b]thiophene-2-carbonyl]benzonitrile;
4-[3-(3,5-difluorobenzyloxy)benzo[b]thiophene-2-carbonyl]benzonitrile;
4-[3-(2,4-difluorobenzyloxy)benzo[b]thiophene-2-carbonyl]benzonitrile;
4-[3-(2,3-difluorobenzyloxy)benzo[b]thiophene-2-carbonyl]benzonitrile;
4-[3-(4-methanesulfonylbenzyloxy)benzo[b]thiophene-2-carbonyl]benzonitrile;
4-[3-(4-iodobenzyloxy)benzo[b]thiophene-2-carbonyl]benzonitrile;
4-{3-[2-(4-chlorophenyl)-2-oxoethoxy]benzo[b]thiophene-2-carbonyl}benzonitrile;
4-[3-(2-oxo-2-phenylethoxy)benzo[b]thiophene-2-carbonyl]benzonitrile;
4-{3-[2-(2-methoxyphenyl)-2-oxoethoxy]benzo[b]thiophene-2-carbonyl}benzonitrile;
4-[3-(2-biphenyl-4-yl-2-oxoethoxy)benzo[b]thiophene-2-carbonyl]benzonitrile;

4-[3-(2-oxo-2-p-tolylethoxy)benzo[b]thiophene-2-carbonyl]benzonitrile;
4-{3-[2-(4-methoxyphenyl)-2-oxoethoxy]benzo[b]thiophene-2-carbonyl}benzonitrile;
4-[3-(2-adamantan-1-yl-2-oxoethoxy)benzo[b]thiophene-2-carbonyl]benzonitrile;
4-{3-[2-(4-fluorophenyl)-2-oxoethoxy]benzo[b]thiophene-2-carbonyl}benzonitrile;
4-{3-[2-(3-methoxyphenyl)-2-oxoethoxy]benzo[b]thiophene-2-carbonyl}benzonitrile;
4-{3-[2-(2-benzyloxyphenyl)-2-oxoethoxy]benzo[b]thiophene-2-carbonyl}benzonitrile;
4-{3-[2-(4-benzyloxyphenyl)-2-oxoethoxy]benzo[b]thiophene-2-carbonyl}benzonitrile;
4-{3-[2-(3,4-dimethoxyphenyl)-2-oxoethoxy]benzo[b]thiophene-2-carbonyl}benzonitrile;
4-{3-[2-(2,4-dimethoxyphenyl)-2-oxoethoxy]benzo[b]thiophene-2-carbonyl}benzonitrile;
4-[3-(2-naphthalen-2-yl-2-oxoethoxy)benzo[b]thiophene-2-carbonyl]benzonitrile;
4-{3-[2-(4-benzyloxy-3-methoxyphenyl)-2-oxoethoxy]benzo[b]thiophene-2-carbonyl}-benzonitrile;
4-{3-[2-(2-benzyloxy-5-fluorophenyl)-2-oxoethoxy]benzo[b]thiophene-2-carbonyl}-benzonitrile;
(3-hydroxybenzofuran-2-yl)phenylmethanone;
2-(2-benzoylbenzofuran-3-yloxy)-1-(4-chlorophenyl)ethanone;
2-(2-benzoylbenzofuran-3-yloxy)-1-(2-methoxyphenyl)ethanone;
2-(2-benzoylbenzofuran-3-yloxy)-1-biphenyl-4-ylethanone;
2-(2-benzoylbenzofuran-3-yloxy)-1-p-tolylethanone;
2-(2-benzoylbenzofuran-3-yloxy)-1-(4-methoxyphenyl)ethanone;
1-adamantan-1-yl-2-(2-benzoylbenzofuran-3-yloxy)ethanone;
2-(2-benzoylbenzofuran-3-yloxy)-1-(4-fluorophenyl)ethanone;
methyl 2-(2-benzoylbenzofuran-3-yloxy)-3-methoxypropionate;
2-(2-benzoylbenzofuran-3-yloxy)-1-(2-benzyloxyphenyl)ethanone;
2-(2-benzoylbenzofuran-3-yloxy)-1-(4-benzyloxyphenyl)ethanone;
2-(2-benzoylbenzofuran-3-yloxy)-1-(3,4-dimethoxyphenyl)ethanone;
2-(2-benzoylbenzofuran-3-yloxy)-1-(2,4-dimethoxyphenyl)ethanone;
2-(2-benzoylbenzofuran-3-yloxy)-1-naphthalen-2-ylethanone;

and also the stereoisomers thereof, the racemates thereof and the pharmaceutically acceptable salts.

18. Process for the preparation of the compounds of the formula (I) according to claim 1, comprising the step consisting in using the compound of the formula (IV):

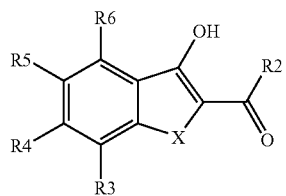

on a halo derivative (V):

Hal-R₁ in equimolar amount, in a polar solvent, at a temperature of between −20 and 200° C.

19. Process according to claim 18, for which the said compound of the formula (IV) is prepared by addition of the corresponding derivative of the formula (II):

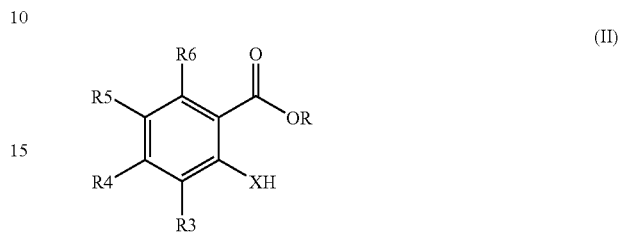

in which R represents a hydrogen atom or an alkyl radical, to a 2-haloethanone derivative of the formula (III):

in which Hal represents a halogen atom, and, in a polar solvent, at a temperature of from −20 to 200° C., followed by cyclization in a polar solvent at a temperature of from −20 to 200° C.

20. Process for the preparation of the compounds of the formula (I) according to claim 18, for which the said polar solvent is chosen from: ethanol, methanol, water, DMF, NMP, DMSO, iPrOH.

21. A pharmaceutical composition comprising a compound of the formula (I):

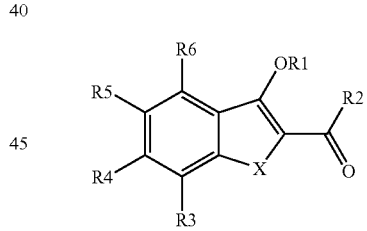

in which:
X=O or S;
R1 is chosen from:
 Alk-COOH,
 Alk-C(=O)—(O)$_m$—Ar,
 Alk-C(=O)—(O)$_m$-Het,
 Alk-C(=O)—(O)$_m$-Alk,
 Alk-C(=O)—(O)$_m$-cycloalkyl,
 Alk-C(=O)NRR',
 Alk-(O)$_m$—Ar,
 Alk-O-Alk,
 Alk-O-Alk-Ar,
 Alk-O-Het,
R2 is chosen from -Alk, —Ar and -cycloalkyl;
R3, R4, R5 and R6, which may be identical or different, are chosen independently from H, -Hal, —OH, -Alk, —OAlk, —CN, —CF₃, —NRR' and —NO₂;

in which, in the definitions of R1-R6:
each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;
each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;
R and R' are chosen independently from H and Alk;
m=0 or 1;
or the stereoisomers, racemates or pharmaceutically acceptable salts thereof, and a pharmaceutically carrier.

22. A method for treating hyperglycaemia, comprising administering to a host in need thereof an effective amount of a compound of the formula (I):

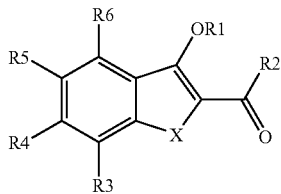

in which:
X=O or S;
R1 is chosen from:
Alk-COOH,
Alk-C(=O)—(O)$_m$—Ar,
Alk-C(=O)—(O)$_m$-Het,
Alk-C(=O)—(O)$_m$-Alk,
Alk-C(=O)—(O)$_m$-cycloalkyl,
Alk-C(=O)NRR',
Alk-(O)$_m$—Ar,
Alk-O-Alk,
Alk-O-Alk-Ar,
Alk-O-Het,
R2 is chosen from -Alk, —Ar and -cycloalkyl;
R3, R4, R5 and R6, which may be identical or different, are chosen independently from H, -Hal, —OH, -Alk, —OAlk, —CN, —CF$_3$, —NRR' and —NO$_2$;
in which, in the definitions of R1-R6:
each of the Alk, which may be identical or different, is optionally and independently substituted by one or more groups chosen from -Hal, —OAlk, —Ar, —OAlkAr, —OH, —CN, —OAr, —CF$_3$, —COOH, —NRR', —C(=O)—(O)$_m$Alk, -Het and —NO$_2$;
each of the Ar, which may be identical or different, is optionally and independently substituted by one or more groups chosen from -Hal, —OAlk, -Alk, —Ar, —OAlkAr, —OH, —CN, —OAr, —CF$_3$, -AlkAr, —COOH, —C(=O)—(O)$_m$Alk, -Alk-C(=O)—(O)$_m$-Alk, —NRR', -Het, —NO$_2$, —S(O)$_n$Ar and —S(O)$_n$Alk;
R and R' are chosen independently from H and Alk;
m=0 or 1,
or stereoisomers, racemates or pharmaceutically acceptable salts thereof.

23. A method according to claim 22, comprising treating diabetes.

24. A method according to claim 22, comprising treating non-insulin-dependent diabetes.

25. A method according to claim 22, comprising treating dyslipidaemia and/or obesity.

26. A method according to claim 22, comprising treating diabetes-related microvascular or macrovascular complications.

27. A method according to claim 26, the microvascular and macrovascular complications are atherosclerosis, arterial hypertension, inflammatory processes, macroangiopathy, microangiopathy, retinopathy or neuropathy.

* * * * *

UNITED STATES PATENT AND TRADEMARK OFFICE
CERTIFICATE OF CORRECTION

PATENT NO. : 7,371,774 B2  Page 1 of 1
APPLICATION NO. : 10/579996
DATED : May 13, 2008
INVENTOR(S) : Gerard Moinet It is certified that error appears in the above-identified patent and that said Letters Patent is hereby corrected as shown below:

Column 82, line 32, reads "Alk, —$CH_2$—OHet," should read -- Alk, —$CH_2$—O—Alk—Ar or —$CH_2$—OHet, --
Column 82, line 34, reads "—O-Alk-Ar,—C" should read -- —O-Alk-Ar, —C --
Column 82, line 44, reads "-Alk-C(=O) —$(O)_n$-Alk, —$S(O)_m$—Ar," should read -- -Alk-C(=O) —$(O)_m$-Alk, —$S(O)_n$—Ar, --
Column 82, line 45, reads "—$S(O)_m$-Alk," should read -- —$S(O)_n$-Alk, --
Column 87, line 16, reads "or the stereoisomers," should read -- or stereoisomers, --
Column 87, line 17, reads "pharmaceutically carrier." should read -- pharmaceutically acceptable carrier. --
Column 88, line 35, reads "claim 26, the microvascular" should read -- claim 26, wherein the microvascular --

Signed and Sealed this

Twenty-eighth Day of April, 2009

JOHN DOLL
*Acting Director of the United States Patent and Trademark Office*